US011034720B2

(12) United States Patent
Chou et al.

(10) Patent No.: US 11,034,720 B2
(45) Date of Patent: Jun. 15, 2021

(54) THIOL-YNE BASED PEPTIDE STAPLING AND USES THEREOF

(71) Applicant: UNIVERSITY OF UTAH RESEARCH FOUNDATION, Salt Lake City, UT (US)

(72) Inventors: Danny Hung-Chieh Chou, Salt Lake City, UT (US); Yuanxiang Wang, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/316,989

(22) PCT Filed: Jul. 17, 2017

(86) PCT No.: PCT/US2017/042406
§ 371 (c)(1),
(2) Date: Jan. 10, 2019

(87) PCT Pub. No.: WO2018/017485
PCT Pub. Date: Jan. 25, 2018

(65) Prior Publication Data
US 2019/0292218 A1 Sep. 26, 2019

Related U.S. Application Data

(60) Provisional application No. 62/363,322, filed on Jul. 17, 2016.

(51) Int. Cl.
*A61K 38/00* (2006.01)
*C07K 1/00* (2006.01)
*C07K 1/113* (2006.01)
*C07K 14/47* (2006.01)
*C07K 14/605* (2006.01)
*C07K 7/00* (2006.01)

(52) U.S. Cl.
CPC .............. *C07K 1/006* (2013.01); *C07K 1/113* (2013.01); *C07K 7/00* (2013.01); *C07K 14/4705* (2013.01); *C07K 14/4748* (2013.01); *C07K 14/605* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,192,713 B1 | 3/2007 | Verdine et al. | |
| 7,723,469 B2 | 5/2010 | Walensky et al. | |
| 7,786,072 B2 | 8/2010 | Verdine et al. | |
| 9,931,579 B1 | 4/2018 | Lin et al. | |
| 2006/0008848 A1 | 1/2006 | Verdine et al. | |
| 2009/0011986 A1 | 1/2009 | Joshi et al. | |
| 2009/0137456 A1 | 5/2009 | Dimarchi et al. | |
| 2009/0149630 A1 | 6/2009 | Walensky et al. | |
| 2009/0176964 A1 | 7/2009 | Walensky et al. | |
| 2010/0081611 A1 | 4/2010 | Bradner et al. | |
| 2010/0168388 A1 | 7/2010 | Bernal et al. | |
| 2010/0184645 A1 | 7/2010 | Verdine et al. | |
| 2011/0172126 A1 | 7/2011 | Brust | |
| 2012/0270800 A1 | 10/2012 | Verdine et al. | |
| 2013/0190504 A1 | 7/2013 | David et al. | |
| 2013/0197189 A1 | 8/2013 | Aimetti et al. | |
| 2014/0357841 A1 | 12/2014 | Li et al. | |
| 2015/0376227 A1 | 12/2015 | Verdine et al. | |

FOREIGN PATENT DOCUMENTS

| | | |
|---|---|---|
| EP | 0467699 A2 | 1/1992 |
| WO | WO-1998/030575 A1 | 7/1998 |
| WO | WO-2005/044839 A2 | 5/2005 |
| WO | WO-2008/061192 A2 | 5/2008 |
| WO | WO-2008/076904 A1 | 6/2008 |
| WO | WO-2008/095063 A1 | 8/2008 |
| WO | WO-2008/121767 A2 | 10/2008 |
| WO | WO-2010/011313 A2 | 1/2010 |
| WO | WO-2011/156686 A2 | 12/2011 |
| WO | WO-2013/123267 A1 | 8/2013 |
| WO | WO-2014/052650 A2 | 4/2014 |
| WO | WO-2014/083505 A1 | 6/2014 |
| WO | WO-2016/209978 A2 | 12/2016 |
| WO | WO-2018/017485 A1 | 1/2018 |

OTHER PUBLICATIONS

Hoyle et al., "Thiol-Ene Click Chemistry" Angew. Chem. Int. Ed., 2010, 49, 1540-1573. (2010).

Non Final Rejection dated Jun. 17, 2019 by the USPTO for U.S. Appl. No. 15/739,626, filed Dec. 22, 2017 and published as US 2019/0092810 A1 on Mar. 28, 2019 (Inventor—Danny Hung-Chieh Chou) (8 pages).

Almarasson, Ö. et al., Crystal Engineering of the Composition of Pharmaceutical Phases. Do Pharmaceutical Co-Crystals Represent a New Path to improved Medicines? Chem Commun. 2004; 35(17):1889-96.

(Continued)

Primary Examiner — Jeanette M Lieb
(74) Attorney, Agent, or Firm — Ballard Spahr LLP

(57) ABSTRACT

In one aspect, the invention relates to compositions comprising stapled peptides, methods of making same, pharmaceutical compositions comprising same, and methods of treating various diseases, including, but not limited to, metabolic disorders such as diabetes, and cancers. The disclosed compounds comprise stapled peptides, including, but not limited to, stapled glucagon, axin, and p53 peptide homologues, which are useful as therapeutic agents for a variety of diseases as disclosed herein. The disclosed methods are useful in the preparation of a variety of stapled peptides, including stapled peptide homologues of glucagon, axin, and p53. This abstract is intended as a scanning tool for purposes of searching in the particular art and is not intended to be limiting of the present invention.

18 Claims, 19 Drawing Sheets
Specification includes a Sequence Listing.

(56) References Cited

OTHER PUBLICATIONS

Bernal, F. et al., Reactivation of the p53 Tumor Suppressor Pathway by a Stapled p53 Peptide. J Am Chem Soc. 2007; 129(9):2456-7.
Bernal, F. et al., A Stapled p53 Helix Overcomes HDMX-Mediated Suppression of p53. Cancer Cell. 2010; 18(5):411-22.
Blackwell, H.E. and Grubbs, R.H., Highly Efficient Synthesis of Covalently Cross-Linked Peptide Helices by Ring-Closing Metathesis. Angew Chem Int Ed. 1998; 37(23):3281-4.
Brown, S.P. and Smith, A.B., Peptide/Protein Stapling and Unstapling: Introduction to s-Tetrazine, Photochemical Release, and Regeneration of the Peptide/Protein. J Am Chem Soc. 2015; 137(12):4034-7.
Chen, Y.H. et al., Determination of the Helix and $\beta$ Form of Proteins in Aqueous Solution by Circular Dichroism. Biochemistry. 1974; 13(16):3350-9.
Cromm, P.M. et al., Hydrocarbon Stapled Peptides as Modulators of Biological Function. ACS Chem Biol. 2015; 10(6):1362-75.
De Araujo, A.D. et al., Comparative a-Helicity of Cyclic Pentapeptides in Water. Angew Chem Int Ed. 2014; 53(27):6965-9.
Grossman, T.N. et al., Inhibition of Oncogenic Wnt Signaling Through Direct Targeting of $\beta$-Catenin. Proc Natl Acad Sci USA. 2012; 109(44):17942-7.
Haney, C.M. et al., Promoting Peptide a-Helix Formation with Dynamic Covalent Oxime Side-Chain Cross-Links. Chem Commun. 2011; 47(39):10915-7.
Hoppmann, C. et al., Intramolecular Bridges Formed by Photoswitchable click Amino Acids. Bielstein J Org Chem. 2012; 8:884-9.
Jo, H. et al., Development of a-Helical Calpain Probes by Mimicking a Natural Protein-Protein Interaction. J Am Chem Soc. 2012; 134(42):17704-13.
Kim, Y.-W. et al., Synthesis of All-Hydrocarbon Stapled a-Helical Peptides by Ring-Closing Olefin Metathesis. Nat Protoc. 2011; 6(6):761-71.
Lau, Y.H. et al., Functionalised Staple Linkages for Modulating the Cellular Activity of Stapled Peptides. Chem Sci. 2014; 5(5):1804-9.
Moellering, R.E. et al., Direct Inhibition of the NOTCH Transcription Factor Complex. Nature. 2009; 462(7270):182-8.
Schafmeister, C.E. et al., An All-Hydrocarbon Cross-Linking System for Enhancing the Helicity and Metabolic Stability of Peptides. J Am Chem Soc. 2000; 122(24):5891-2.
Sinclair, J.K.-L. et al., Inhibition Epidermal Growth Factor Receptor at a Distance. J Am Chem Soc. 2014; 136(32):11232-5.
Spokoyny, A.M. et al., A Perfluoroaryl-cysteine S(N)Ar Chemistry Approach to Unprotected Peptide Stapling. J Am Chem Soc. 2013; 135(16):5946-9.
Timmerman, P. et al., Rapid and Quantitative Cyclization of Multiple Peptide Loops onto Synthetic Scaffolds for Structural Mimicry of Protein Surfaces. ChemBioChem. 2005; 6(5):821-4.
Timmerman, P. et al., Functional Reconstruction and Synthetic Mimicry of a Conformational Epitope Using CLIPS Technology. J Mol Recgonit. 2007; 20(5):283-99.
Walensky, L.D. et al., Activation of Apoptosis in Vivo by a Hydrocarbon-Stapled BH3 Helix. Science. 2004; 305(5689):1466-70.
Walensky, L.D. and Bird, G.H., Hydrocarbon-Stapled Peptides: Principles, Practice, and Progress. J Med Chem. 2014; 57(15):6275-88.
Wang, Y. and Chou, D.H.-C., A Thiol-Ene Coupling Approach to Native Peptide Stapling and Macrocyclization. Angew Chem Int Ed. 2015; 54(37):10931-4.
Supplementary European Search Report dated Jan. 16, 2019 by the European Patent Office for Patent Application No. 16815225.4, filed Jan. 22, 2018 and published as EP 3310373 on Apr. 25, 2018 (Inventor—Chou et al.; Applicant—University of Utah Research Foundation) (10 pages).
International Search Report and Written Opinion dated Jan. 10, 2017 by the International Searching Authority for Patent Application No. PCT/US2016/038788, filed Jun. 22, 2016 and published as WO 2016/209978 on Dec. 29, 2016 (Inventor—Chou et al.; University of Utah Research Foundation) (20 pages).
International Preliminary Report on Patentability dated Dec. 26, 2017 by the International Searching Authority for Patent Application No. PCT/US2016/038788, filed Jun. 22, 2016 and published as WO 2016/209978 on Dec. 29, 2016 (Inventor—Chou et al.; University of Utah Research Foundation) (14 pages).
Restriction Requirement dated Jan. 15, 2019 by the U.S. Patent and Trademark Office for U.S. Appl. No. 15/739,626, filed Dec. 22, 2017 (Inventor—Chou et al.; Applicant—University of Utah Research Foundation) (9 pages).
International Search Report and Written Opinion dated Dec. 14, 2017 by the International Searching Authority for Patent Application No. PCT/US2017/042406, filed Jul. 17, 2017 and published as WO 2018/017485 on Jan. 25, 2018 (Inventor—Chou et al.; Applicant—University of Utah Research Foundation) (15 pages).
International Preliminary Report on Patentability dated Jan. 22, 2019 by the International Searching Authority for Patent Application No. PCT/US2017/042406, filed Jul. 17, 2017 and published as WO 2018/017485 on Jan. 25, 2018 (Inventor—Chou et al.; Applicant—University of Utah Research Foundation) (10 pages).
Response to Non-final Office Action filed on Dec. 16, 2019 with the USPTO for U.S. Appl. No. 15/739,626, filed Dec. 22, 2017 and published as US 2019/0092810 A1 on Mar. 28, 2019 (Inventor—Danny Hung-Chieh Chou) (14 pages).
Non Final Rejection dated Apr. 1, 2020 by the USPTO for U.S. Appl. No. 15/739,626, filed Dec. 22, 2017 and published as US 2019/0092810 A1 on Mar. 28, 2019 (Inventor—Danny Hung-Chieh Chou) (8 pages).
Yu, et al. (2015) "Sequential Michael addition thiol-ene and radical-mediated thiol-ere reactions in one-pot produced sequence-ordered polymers," *Polymer Chemistry* 6: 1527-1532.
Non Final Rejection issued on Dec. 15, 2020 by the USPTo for U.S. Appl. No. 15/739,626, which was filed on Dec. 22, 2017 and published as U.S. 2019/0092810 A1 on Mar. 28, 2019 (Inventor-Danny Hung-Chieh Chou) (10 pages).

LC-Chromatogram for P-QSQ+diyne (ZZ isomer)

LC-Chromatogram for P-QSQ+diyne (left isomer)

MS-Spectrum for P-QSQ+diyne+Cysteine

LC-Chromatogram for P-QSQ+diyne+Cysteine

MS-Spectrum for P-QSQ+diyne+Glutathione

LC-Chromatogram for P-QSQ+diyne+Glutathione

MS-Spectrum for FITC-QSQ+1,8diene

LC-Chromatogram for FITC-QSQ+1,8diene

MS-Spectrum for FITC-QSQ+diyne

LC-Chromatogram for FITC-QSQ+diyne

MS-Spectrum for YLP+Diyne

LC-Chromatogram for YLP+diyne

MS-Spectrum for YLP+Diyne+CRRRRC

LC-Chromatogram for YLP+diyne+CRRRRC

LC-Chromatogram for YLC

MS-Spectrum for YLC+diyne

LC-Chromatogram for YLC+diyne

MS-Spectrum for YLC+diyne+CRRRRC

LC-Chromatogram for YLC+diyne+CRRRRC

SEQUENCE LISTING

```
<160> NUMBER OF SEQ ID NOS: 27

<210> SEQ ID NO 1
<211> LENGTH: 29
<212> TYPE: PRT
<213> ORGANISM: Artificial Sequence
<220> FEATURE:
<223> OTHER INFORMATION: Synthetic construct

<400> SEQUENCE: 1

His Ser Gln Gly Thr Phe Thr Ser Asp Tyr Ser Lys Tyr Leu Asp Ser
1               5                   10                  15

Cys Arg Ala Gln Cys Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
```

<223> OTHER INFORMATION: Synthetic construct

<400> SEQUENCE: 2

His Ser Gln Gly Thr Phe Thr Ser Asp Tyr Ser Lys Tyr Leu Asp Ser
1               5                   10                  15

Arg Arg Ala Cys Asp Phe Val Cys Trp Leu Met Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic construct

<400> SEQUENCE: 3

His Ser Gln Gly Thr Phe Thr Ser Asp Tyr Ser Lys Tyr Leu Asp Ser
1               5                   10                  15

Arg Arg Ala Cys Asp Phe Val Gln Trp Leu Cys Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic construct

<400> SEQUENCE: 4

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Cys Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic construct

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Met Cys Thr
            20                  25

<210> SEQ ID NO 6
<211> LENGTH: 16
<212> TYPE: PRT
<213> ORGANISM: Artificial Sequence
<220> FEATURE:
<223> OTHER INFORMATION: Synthetic construct

<400> SEQUENCE: 6

His Ser Gln Gly Thr Phe Thr Ser Asp Tyr Ser Lys Tyr Leu Asp Ser
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Synthetic construct

```
<400> SEQUENCE: 7

Phe Val Gln Trp Leu Met Asn Thr
1               5

<210> SEQ ID NO 8
<211> LENGTH: 19
<212> TYPE: PRT
<213> ORGANISM: Artificial Sequence
<220> FEATURE:
<223> OTHER INFORMATION: Synthetic construct

<400> SEQUENCE: 8

His Ser Gln Gly Thr Phe Thr Ser Asp Tyr Ser Lys Tyr Leu Asp Ser
1               5                   10                  15

Arg Arg Ala

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Trp Leu Met Asn Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic construct

<400> SEQUENCE: 10

Asp Phe Val Gln Trp Leu
1               5

<210> SEQ ID NO 11
<211> LENGTH: 20
<212> TYPE: PRT
<213> ORGANISM: Artificial Sequence
<220> FEATURE:
<223> OTHER INFORMATION: Synthetic construct

<400> SEQUENCE: 11

His Ser Gln Gly Thr Phe Thr Ser Asp Tyr Ser Lys Tyr Leu Asp Ser
1               5                   10                  15

Arg Arg Ala Gln
            20

<210> SEQ ID NO 12
<211> LENGTH: 6
<212> TYPE: PRT
<213> ORGANISM: Artificial Sequence
<220> FEATURE:
<223> OTHER INFORMATION: Synthetic construct

<400> SEQUENCE: 12

Phe Val Gln Trp Leu Met
1               5

<210> SEQ ID NO 13
<211> LENGTH: 23
<212> TYPE: PRT
```

```
<213> ORGANISM: Artificial Sequence
<220> FEATURE:
<223> OTHER INFORMATION: Synthetic construct

<400> SEQUENCE: 13

His Ser Gln Gly Thr Phe Thr Ser Asp Tyr Ser Lys Tyr Leu Asp Ser
1               5                   10                  15

Arg Arg Ala Gln Asp Phe Val
            20

<210> SEQ ID NO 14
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 14

Gln Ser Gln Gln Thr Phe Cys Asn Leu Trp Arg Leu Leu Cys Gln Asn
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: AMIDATION
<220> FEATURE:
<221> NAME/KEY: MISC_FEATURE
<222> LOCATION: (7)..(7)
<223> OTHER INFORMATION: cysteine residue is attached to a thiol group
<220> FEATURE:
<221> NAME/KEY: MISC_FEATURE
<222> LOCATION: (14)..(14)
<223> OTHER INFORMATION: cysteine residue is attached to a thiol group
<220> FEATURE:
<221> NAME/KEY: MOD_RES
<222> LOCATION: (16)..(16)
<223> OTHER INFORMATION: AMIDATION

<400> SEQUENCE: 15

Gln Ser Gln Gln Thr Phe Cys Asn Leu Trp Arg Leu Leu Cys Gln Asn
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: cysteine residue is attached to a thiol group
<220> FEATURE:
<221> NAME/KEY: MISC_FEATURE
```

<222> LOCATION: (14)..(14)
<223> OTHER INFORMATION: cysteine residue is attached to a thiol group
<220> FEATURE:
<221> NAME/KEY: MOD_RES
<222> LOCATION: (16)..(16)
<223> OTHER INFORMATION: AMIDATION

<400> SEQUENCE: 16

Gln Ser Gln Gln Thr Phe Cys Asn Leu Trp Arg Leu Leu Cys Gln Asn
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: alanine is beta-alanine
<220> FEATURE:
<221> NAME/KEY: MOD_RES
<222> LOCATION: (17)..(17)
<223> OTHER INFORMATION: AMIDATION

<400> SEQUENCE: 17

Ala Gln Ser Gln Gln Thr Phe Cys Asn Leu Trp Arg Leu Leu Cys Gln
1               5                   10                  15

Asn

<210> SEQ ID NO 18
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: alanine is beta-alanine
<220> FEATURE:
<221> NAME/KEY: MISC_FEATURE
<222> LOCATION: (8)..(8)
<223> OTHER INFORMATION: Cysteine residue is attached to a thiol group
<220> FEATURE:
<221> NAME/KEY: MISC_FEATURE
<222> LOCATION: (15)..(15)
<223> OTHER INFORMATION: Cysteine residue is attached to a thiol group
<220> FEATURE:
<221> NAME/KEY: MOD_RES
<222> LOCATION: (17)..(17)
<223> OTHER INFORMATION: AMIDATION

<400> SEQUENCE: 18

Ala Gln Ser Gln Gln Thr Phe Cys Asn Leu Trp Arg Leu Leu Cys Gln
1               5                   10                  15

Asn

<210> SEQ ID NO 19
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Alanine is beta alanine
<220> FEATURE:
<221> NAME/KEY: MISC_FEATURE

```
<222> LOCATION: (8)..(8)
<223> OTHER INFORMATION: Cysteine residue is attached to a thiol group
<220> FEATURE:
<221> NAME/KEY: MISC_FEATURE
<222> LOCATION: (15)..(15)
<223> OTHER INFORMATION: Cysteine residue is attached to a thiol group
<220> FEATURE:
<221> NAME/KEY: MOD_RES
<222> LOCATION: (17)..(17)
<223> OTHER INFORMATION: AMIDATION

<400> SEQUENCE: 19

Ala Gln Ser Gln Gln Thr Phe Cys Asn Leu Trp Arg Leu Leu Cys Gln
1               5                   10                  15
Asn

<210> SEQ ID NO 20
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 20

Cys Arg Arg Arg Arg Cys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Cysteine residue is attached to a thiol group
<220> FEATURE:
<221> NAME/KEY: MOD_RES
<222> LOCATION: (6)..(6)
<223> OTHER INFORMATION: AMIDATION
<220> FEATURE:
<221> NAME/KEY: MISC_FEATURE
<222> LOCATION: (6)..(6)
<223> OTHER INFORMATION: Cysteine residue is attached to a thiol group

<400> SEQUENCE: 21

Cys Arg Arg Arg Arg Cys
1               5

<210> SEQ ID NO 22
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (15)..(15)
<223> OTHER INFORMATION: AMIDATION
```

```
<400> SEQUENCE: 22

Tyr Leu Pro Phe Ile Met Cys Leu Leu Lys Thr Leu Ala Cys His
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Cysteine residuce is attached to a thiol group
<220> FEATURE:
<221> NAME/KEY: MISC_FEATURE
<222> LOCATION: (14)..(14)
<223> OTHER INFORMATION: Cysteine residuce is attached to a thiol group
<220> FEATURE:
<221> NAME/KEY: MOD_RES
<222> LOCATION: (15)..(15)
<223> OTHER INFORMATION: AMIDATION

<400> SEQUENCE: 23

Tyr Leu Pro Phe Ile Met Cys Leu Leu Lys Thr Leu Ala Cys His
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Cysteine residue is attached to a thiol group
<220> FEATURE:
<221> NAME/KEY: MISC_FEATURE
<222> LOCATION: (14)..(14)
<223> OTHER INFORMATION: Cysteine residue is attached to a thiol group
<220> FEATURE:
<221> NAME/KEY: MOD_RES
<222> LOCATION: (15)..(15)
<223> OTHER INFORMATION: AMIDATION

<400> SEQUENCE: 24

Tyr Leu Pro Phe Ile Met Cys Leu Leu Lys Thr Leu Ala Cys His
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 25

Tyr Leu Cys Phe Ile Met Glu Leu Leu Cys Thr Leu Ala Glu His
1               5                   10                  15

<210> SEQ ID NO 26
```

```
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Cysteine residue is attached to a thiol group
<220> FEATURE:
<221> NAME/KEY: MISC_FEATURE
<222> LOCATION: (10)..(10)
<223> OTHER INFORMATION: Cysteine residue is attached to a thiol group
<220> FEATURE:
<221> NAME/KEY: MOD_RES
<222> LOCATION: (15)..(15)
<223> OTHER INFORMATION: AMIDATION

<400> SEQUENCE: 26

Tyr Leu Cys Phe Ile Met Glu Leu Leu Cys Thr Leu Ala Glu His
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Cysteine residue is attached to a thiol group
<220> FEATURE:
<221> NAME/KEY: MISC_FEATURE
<222> LOCATION: (10)..(10)
<223> OTHER INFORMATION: Cysteine residue is attached to a thiol group
<220> FEATURE:
<221> NAME/KEY: MOD_RES
<222> LOCATION: (15)..(15)
<223> OTHER INFORMATION: AMIDATION

<400> SEQUENCE: 27

Tyr Leu Cys Phe Ile Met Glu Leu Leu Cys Thr Leu Ala Glu His
1               5                   10                  15
```

THIOL-YNE BASED PEPTIDE STAPLING AND USES THEREOF

CROSS-REFERENCE TO RELATED APPLICATIONS

This Application is a national stage filing under 35 U.S.C. § 371 of International Application No. PCT/US2017/042406, filed on Jul. 17, 2017, which claims the benefit of U.S. Provisional Application No. 62/363,322, filed on Jul. 17, 2016, the contents of which are incorporated herein by reference in their entireties.

The Sequence Listing submitted on Jan. 21, 2021 as a text file named "21101_0333U2_ST25.txt," created on Jan. 20, 2021, and having a size of 12,288 bytes is hereby incorporated by reference pursuant to 37 C.F.R. § 1.52(e)(5).

BACKGROUND

Peptides have attracted increasing attention as potential therapeutic agents. The biophysical properties of peptides allow for selective biological recognition of receptors, enzymes, and nucleic acids, thereby influencing cell-cell communication and/or controlling vital cellular functions, such as metabolism, immune defense, and cell division. Unfortunately, the utility of peptides as drugs is severely limited by several factors, including their rapid degradation by proteases under physiological conditions, their poor cell permeability, and their lack of binding specificity resulting from conformational flexibility.

Side chain crosslinking ("peptide stapling") is one of the numerous strategies that aim to stabilize and/or mimic peptide helices. Because peptide stapling necessitates macrocyclization, an entropically unfavorable process, very few reactions are known to date that give rise to reasonable yields without undesirable side reactions. One well-described reaction known to yield stapled peptides is based on using olefin-containing amino acids followed by ring-closing metathesis (RCM) (H. E. Blackwell and R. H. Grubbs, Angew. Chem. Int. Ed. 1998, 37, 3281-3284; and C. E. Schafmeister, et al., J. Am. Chem. Soc. 2000, 122, 5891-5892). Since this work, stapled peptides have developed into promising therapeutics to block protein-protein interactions or increase protease resistance (L. D. Walensky and G. H. Bird, J. Med. Chem. 2014, 57, 6275-6288; and P. M. Cromm, et al., ACS Chem. Biol. 2015). The hydrocarbon stapled peptides have been demonstrated in targeting intracellular proteins such as the BCL-2 family proteins (L. D. Walensky, et al., Science 2004, 305, 1466-1470) and NOTCH (R. E. Moellering, et al., Nature 2009, 462, 182-188), as well as extracellular proteins such as EGFR (J. K. Sinclair, et al., J. Am. Chem. Soc. 2014, 136, 11232-11235).

Due to its therapeutic potential, a growing number of studies reported alternative stapling methods such as lactamization (A. D. de Araujo, et al., Angew. Chem. Int. Ed. 2014, 53, 6965-6969), cycloaddition (Y. H. Lau, et al., Chem. Sci. 2014, 5, 1804-1809), oxime formation (C. M. Haney, et al., Chem. Commun. 2011, 47, 10915-10917), thioether (H. Jo, et al., J. Am. Chem. Soc. 2012, 134, 17704-17713; P. Timmerman, et al., ChemBioChem 2005, 6, 821-824; and P. Timmerman, et al., J. Mol. Recognit. 2007, 20, 283-299), and SNAr reaction (A. M. Spokoyny, et al., J Am Chem Soc 2013, 135, 5946-5949; and S. P. Brown and A. B. Smith, 3rd, J Am Chem Soc 2015, 137, 4034-4037). Although some of these methods still require unnatural amino acids (UAAs) in the peptide synthesis, both lactamization and cysteine modification circumvent the use of UAAs and could potentially be applied to recombinantly expressed peptides and proteins. However, the additional amide bond and perfluoroaromatic group may affect the properties of the stapled peptides and lead to unwanted interactions or immunogenic effects. Furthermore, the scope of linker length and types are limited due to the restriction on the ligation reaction.

Despite advances in reaction methods to synthesize stapled peptides, there is still a scarcity of synthetic methods capable of preparing stapled peptides with both the desired peptide properties and ease of synthesis. Additionally, there also exists a need for stapling methods that permit further functionalization of the stapled peptide without modification of the peptide sequence itself. These needs and other needs are satisfied by the present invention.

SUMMARY

In accordance with the purpose(s) of the invention, as embodied and broadly described herein, the invention, in one aspect, relates to compositions comprising stapled peptides, methods of making same, pharmaceutical compositions comprising same, and methods of treating various diseases, including, but not limited to, metabolic disorders such as diabetes, and cancers. The disclosed compounds comprise stapled peptides, including, but not limited to, stapled glucagon, axin, and p53 peptide homologues, which are useful as therapeutic agents for a variety of diseases as disclosed herein. The disclosed methods are useful in the preparation of a variety of stapled peptides, including stapled peptide homologues of glucagon, axin, and p53.

Disclosed are methods of stapling a peptide having two thiol functionalities with a linker having two unstaturated functionalities comprising two alkyne moieties or comprising one alkyne moiety and one alkene moiety, the method comprising a first reacting step of the two thiol functionalities with the two unsaturated functionalities, thereby providing two alkenyl sulfide moieties or thereby providing one alkenyl sulfide moiety and one alkyl sulfide moiety, and optionally, a second reacting step of the one or two alkenyl sulfide moieties with one or two radical agents or one or two nucleophilic agents.

Also disclosed are compounds having a structure represented by a formula:

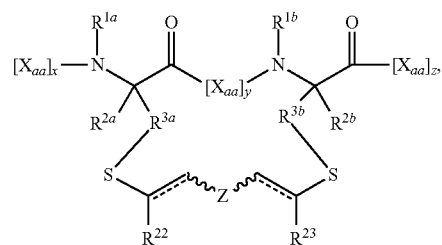

wherein each occurrence of ---- is an optional covalent bond, thereby signifying a single bond or a double bond; wherein each of x and z is independently an integer having a value of 0 to 100; wherein y is an integer having a value of 2 to 10; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0;

wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —(CH$_2$)$_3$—(OCH$_2$CH$_2$)$_q$—O—(CH$_2$)$_3$—, substituted with $R^{22}$ and $R^{23}$, wherein q is 0, 1, 2, 3, or 4; or a moiety represented by a formula:

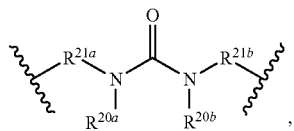

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

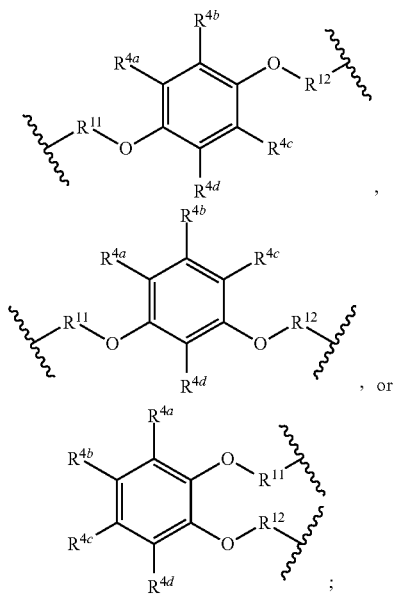

wherein each of $R^{4a}$, $R^{4b}$, $R^{4c}$, and $R^{4d}$ is independently selected from hydrogen, hydroxy, amino, C1-C4 alkyl, and —CO$_2$H; and wherein each of $R^{11}$ and $R^{12}$ is independently C3-C6 alkylene; wherein each of $R^{22}$ and $R^{23}$ is independently selected from: hydrogen when adjacent a double bond and hydrogen or —SR$^{24}$ when adjacent a single bond, provided that both $R^{22}$ and $R^{23}$ are not simultaneously hydrogen adjacent a single bond; wherein each $R^{24}$, when present, is independently selected from hydrogen, C1-C24 alkyl, —(CH$_2$CH$_2$O)$_n$(C1-C4 alkyl), a solubilizing functionality, a labeling functionality, a tether to solid-phase support, or a tether to a second peptide; and wherein each occurrence of n is an integer from 1 to 12, or a pharmaceutically acceptable salt thereof.

Also disclosed are methods of preparing a stapled peptide, the method comprising the steps of: providing a peptide having the structure represented by the formula:

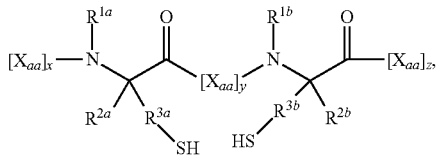

wherein each of x and z is independently an integer having a value of 0 to 100; wherein y is an integer having a value of 1 to 20; wherein each instance of X$_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a linker compound having the structure represented by the formula:

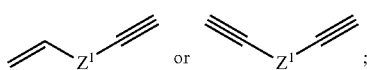

wherein $Z^1$ is C1-C8 alkyl, C3-C8 ether, C6-C8 polyether, or a moiety represented by a formula:

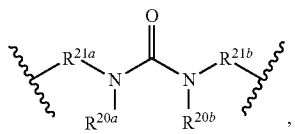

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

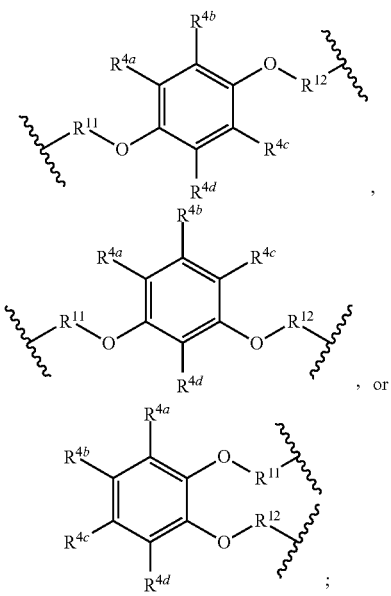

wherein each of $R^{4a}$, $R^{4b}$, $R^{4c}$, and $R^{4d}$ is independently hydrogen, hydroxy, amino, C1-C4 alkyl, and —CO$_2$H; and wherein each of $R^{13}$ and $R^{14}$ is independently C1-C4 alkyl; reacting the peptide and the linker compound; thereby forming the stapled peptide.

Also disclosed are methods of preparing a stapled peptide, the method comprising the steps of: providing a first peptide and a second peptide having, respectively, the structure represented by the formulas:

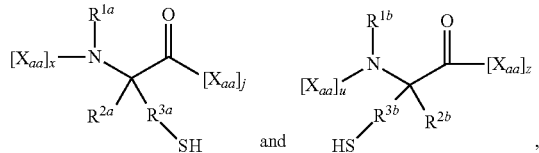

wherein each of j, u, x, and z is independently an integer having a value of 0 to 100; provided that j and x are not simultaneously 0; and provided that u and z are not simultaneously 0; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a linker compound having the structure represented by the formula:

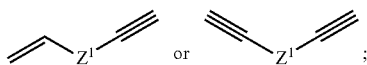

wherein $Z^1$ is C1-C8 alkyl, C3-C8 ether, C6-C8 polyether, or a moiety represented by a formula:

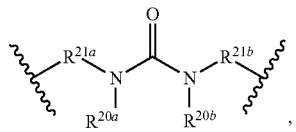

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

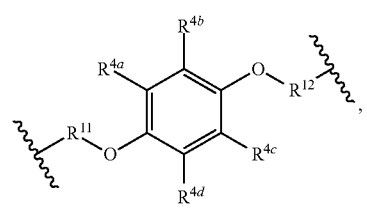

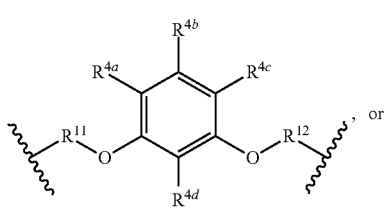

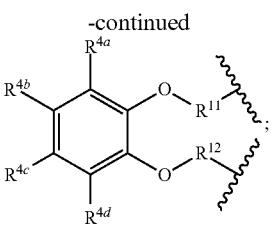

wherein each of $R^{4a}$, $R^{4b}$, $R^{4c}$, and $R^{4d}$ is independently hydrogen, hydroxy, amino, C1-C4 alkyl, and —CO$_2$H; and wherein each of $R^{13}$ and $R^{14}$ is independently C1-C4 alkyl; reacting the peptide and the linker compound; thereby forming the stapled peptide.

Also disclosed are stapled peptides prepared by any of the disclosed methods.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
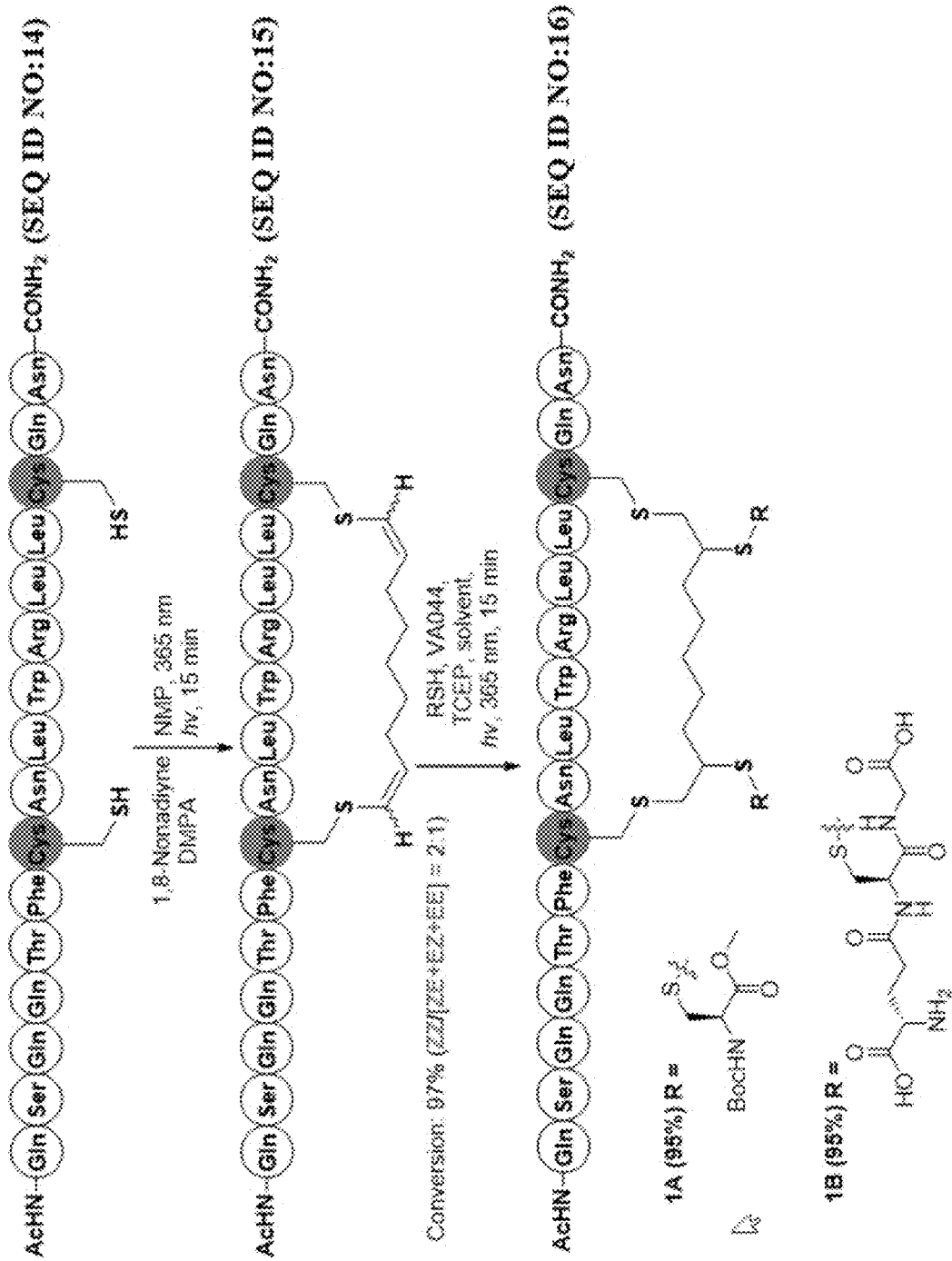
FIG. 1 shows a reaction schematic for a thiol-yne reaction between a peptide and a diyne.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorder, e.g., diabetes or cancer, prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder such as diabetes or cancer) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target of a disclosed peptide, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

"Stapling," as used herein, is a process by which the side-chains of two amino acid residues in a peptide are bonded via a linker compound to generate a cross-link between the two amino acids (a "staple"). Stapling engenders constraint on a secondary structure, such as an alpha helical structure. The length and geometry of the cross-link can be optimized to improve the yield of the desired secondary structure content. The constraint provided can, for example, prevent the secondary structure to unfold and/or can reinforce the shape of the secondary structure, and thus makes the secondary structure more stable. Multiple stapling is also referred to herein as "stitching." See, e.g., U.S. Pat. Nos. 7,192,713; 7,723,469; 7,786,072; U.S. Patent Application Publication Nos: 2010-0184645; 2010-0168388; 2010-0081611; 2009-0176964; 2009-0149630; 2006-0008848; PCT Application Publication Nos: WO 2010/011313; WO 2008/121767; WO 2008/095063; WO 2008/061192; and WO 2005/044839, which depict stapling and stitching of polypeptides. In certain embodiments, stapling may occur at i,i+3, i,i+4, and/or i,i+7 positions of the polypeptide.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbomenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\circ_3$, $-OSiR^\circ_3$, $-C(O)SR^\bullet$, $-(C_{1-4}$ straight or branched alkylene)C(O)OR$^\circ$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_1$ 4 aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

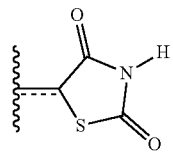

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

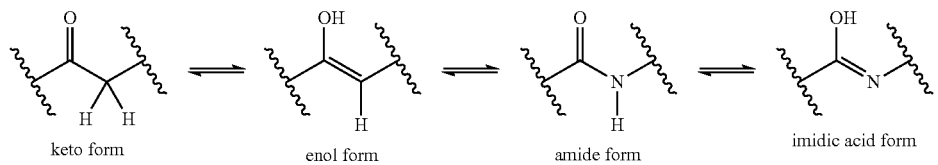 [SMILES: *CC(*)=O ; */C=C(/*)O ; *NC(*)=O ; */N=C(/*)O]

keto form    enol form    amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

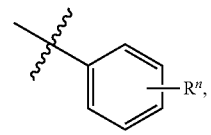

which is understood to be equivalent to a formula:

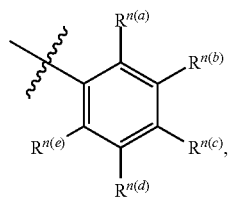

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Peptides

In one aspect, the invention relates to stapled peptide compositions, including, but not limited to, stapled peptide homologues of glucagon, axin, and p53. More specifically, in one aspect, the present invention relates to stapled glucagon peptides.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Stapled Peptide Compositions

In one aspect, the invention relates to a compound having a structure represented by a formula:

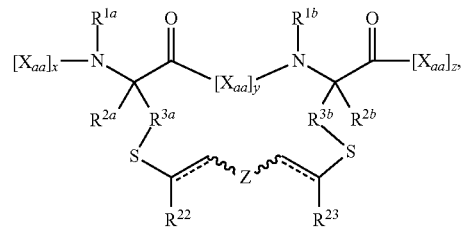

wherein each occurrence of ---- is an optional covalent bond, thereby signifying a single bond or a double bond; wherein each of x and z is independently an integer having a value of 0 to 100; wherein y is an integer having a value of 2 to 10; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —(CH$_2$)$_3$—(OCH$_2$CH$_2$)$_q$—O—(CH$_2$)$_3$—, substituted with $R^{22}$ and $R^{23}$, wherein q is 0, 1, 2, 3, or 4; or a moiety represented by a formula:

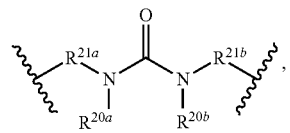

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

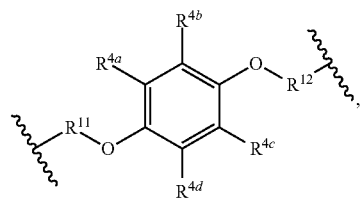

-continued

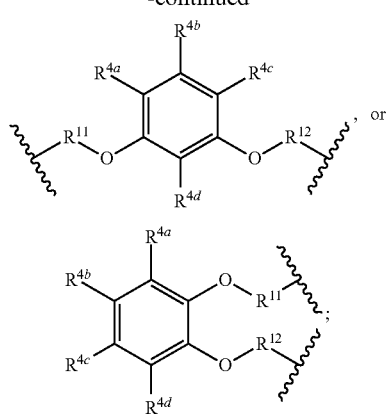

wherein each of $R^{4a}$, $R^{4b}$, $R^{4c}$, and $R^{4d}$ is independently selected from hydrogen, hydroxy, amino, C1-C4 alkyl, and —$CO_2H$; and wherein each of $R^{11}$ and $R^{12}$ is independently C3-C6 alkylene; wherein each of $R^{22}$ and $R^{23}$ is independently selected from: hydrogen when adjacent a double bond and hydrogen or —$SR^{24}$ when adjacent a single bond, provided that both $R^{22}$ and $R^{23}$ are not simultaneously hydrogen adjacent a single bond; wherein each $R^{24}$, when present, is independently selected from hydrogen, C1-C24 alkyl, —$(CH_2CH_2O)_n$(C1-C4 alkyl), a solubilizing functionality, a labeling functionality, a tether to solid-phase support, or a tether to a second peptide; and wherein each occurrence of n is an integer from 1 to 12, or a pharmaceutically acceptable salt thereof.

In a further aspect, Z is a moiety represented by a formula:

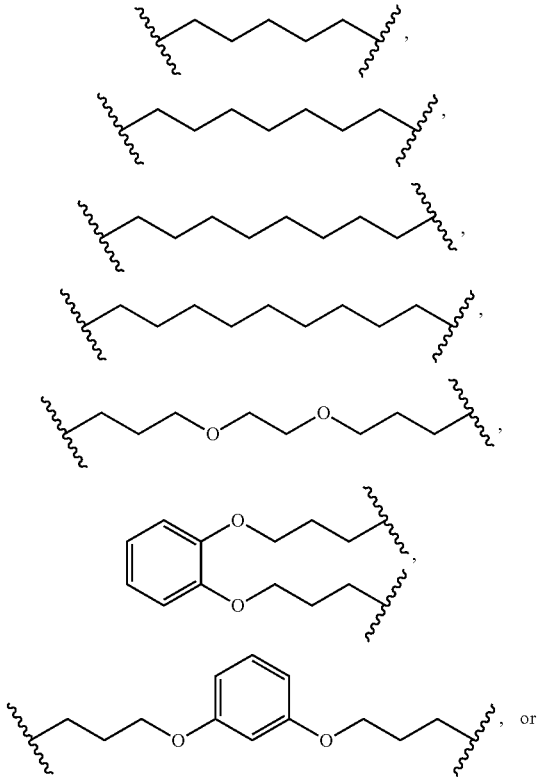

-continued

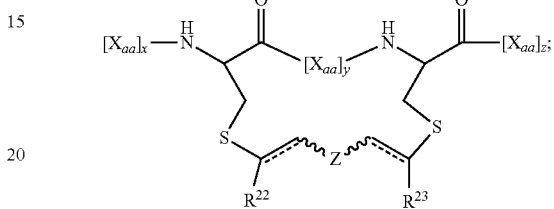

In a further aspect, the compound has a structure represented by a formula:

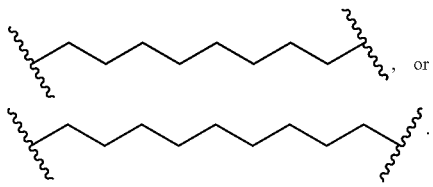

wherein each of x and z is independently an integer having a value of 2 to 15; wherein y is 2, 3, 6 or 10; and wherein Z is a moiety represented by a formula:

In a further aspect, each of x and z is independently an integer having a value of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In various aspects, each of x and z is independently an integer having a value of 0 to 100. In a further aspect, each of x and z is independently an integer having a value of 0 to 90. In a still further aspect, each of x and z is independently an integer having a value of 0 to 80. In a yet further aspect, each of x and z is independently an integer having a value of 0 to 70. In an even further aspect, each of x and z is independently an integer having a value of 0 to 60. In a still further aspect, each of x and z is independently an integer having a value of 0 to 50. In a yet further aspect, each of x and z is independently an integer having a value of 0 to 40. In an even further aspect, each of x and z is independently an integer having a value of 0 to 30. In a still further aspect, each of x and z is independently an integer having a value of 0 to 20. In a yet further aspect, each of x and z is independently an integer having a value of 0 to 10.

In a further aspect, each of x and z is independently an integer having a value of 1 to 15. In a still further aspect, each of x and z is independently an integer having a value of 2 to 15. In a yet further aspect, each of x and z is independently an integer having a value of 3 to 15. In an even further aspect, each of x and z is independently an integer having a value of 4 to 15. In a still further aspect, each of x and z is independently an integer having a value of 5 to 15. In a yet further aspect, each of x and z is independently an integer having a value of 6 to 15. In an even further aspect, each of x and z is independently an integer having a value of 7 to 15. In a still further aspect, each of x and z is independently an integer having a value of 8 to 15. In a yet further aspect, each of x and z is independently an integer having a value of 9 to 15. In an even further aspect, each of x and z is independently an integer having a value of 10 to 15.

In various aspects, y is an integer having a value of 2 to 10. In a further aspect, y is an integer having a value of 2, 3, 6 or 10.

In a further aspect, y is an integer having a value of 2. In a still further aspect, y is an integer having a value of 3. In a yet further aspect, y is an integer having a value of 4. In an even further aspect, y is an integer having a value of 5. In a still further aspect, y is an integer having a value of 6. In a yet further aspect, y is an integer having a value of 7. In an even further aspect, y is an integer having a value of 8. In a still further aspect, y is an integer having a value of 9. In a yet further aspect, y is an integer having a value of 10.

In various aspects, q is 0, 1, 2, 3, or 4. In a further aspect, q is 0, 1, 2, or 3. In a still further aspect, q is 0, 1, or 2. In a yet further aspect, q is 0 or 1. In a yet further aspect, q is 0. In a still further aspect, q is 1. In a yet further aspect, q is 2. In a yet further aspect, q is 3. In an even further aspect, q is 4.

In one aspect, the invention relates to a compound having a structure represented by a formula:

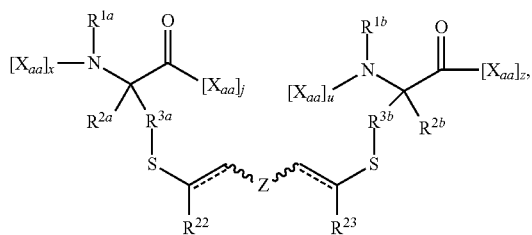

wherein each occurrence of --- is an optional covalent bond, thereby signifying a single bond or a double bond; wherein each of j, u, x, and z is independently an integer having a value of 0 to 100; provided that j and x are not simultaneously 0; and provided that u and z are not simultaneously 0; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —(CH$_2$)$_3$—(OCH$_2$CH$_2$)$_q$—O—(CH$_2$)$_3$—, wherein q is 0, 1, 2, 3, or 4; or a moiety represented by a formula:

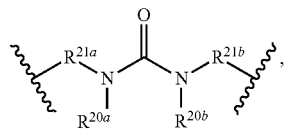

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

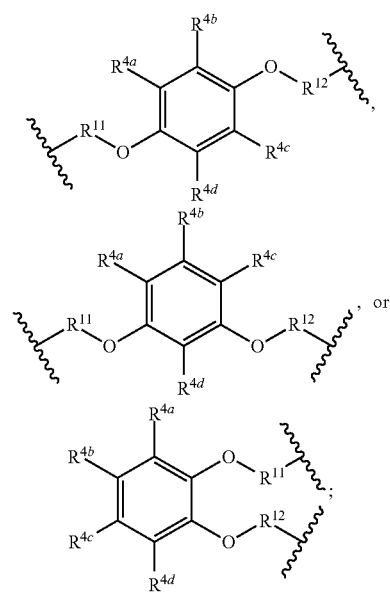

wherein q is 0, 1, 2, 3, or 4; wherein each of $R^{4a}$, $R^{4b}$, $R^{4c}$, and $R^{4d}$ is independently hydrogen, hydroxy, amino, C1-C4 alkyl, and —CO$_2$H; and wherein each of $R^{11}$ and $R^{12}$ is independently C3-C6 alkylene; wherein each of $R^{22}$ and $R^{23}$ is independently selected from: hydrogen when adjacent a double bond and hydrogen or —SR$^{24}$ when adjacent a single bond, provided that both $R^{22}$ and $R^{23}$ are not simultaneously hydrogen adjacent a single bond; wherein each $R^{24}$, when present, is independently selected from hydrogen, C1-C24 alkyl, —(CH$_2$CH$_2$O)$_n$(C1-C4 alkyl), a solubilizing functionality, a labeling functionality, a tether to solid-phase support, or a tether to a second peptide; and wherein each occurrence of n is an integer from 1 to 12, or a pharmaceutically acceptable salt thereof.

In a further aspect, Z is a moiety represented by a formula:

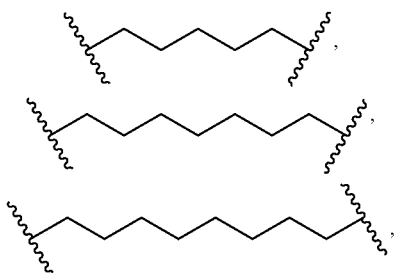

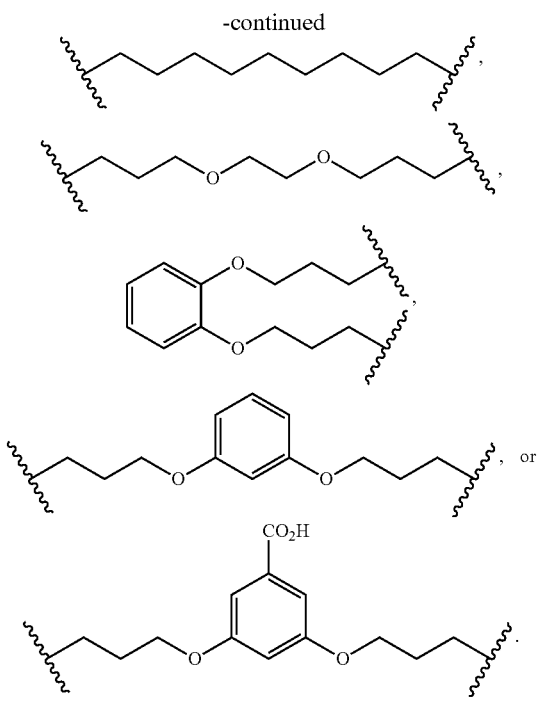

In a further aspect, the compound has a structure represented by a formula:

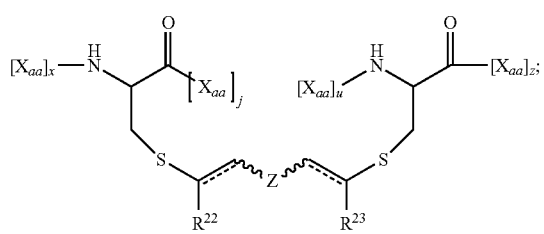

wherein each of x and z is independently an integer having a value of 2 to 15; wherein y is 2, 3, 6 or 10; and wherein Z is a moiety represented by a formula:

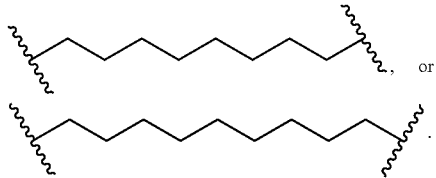

In various aspects, each of j, u, x, and z is independently an integer having a value of 0 to 100; provided that j and x are not simultaneously 0; and provided that u and z are not simultaneously 0. In a further aspect, x has the same value as u; and j has the same value as z.

In a further, each of j, u, x, and z is independently an integer having a value of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In various aspects, each of j, u, x, and z is independently an integer having a value of 0 to 100. In a further aspect, each of j, u, x, and z is independently an integer having a value of 0 to 90. In a still further aspect, each of j, u, x, and z is independently an integer having a value of 0 to 80. In a yet further aspect, each of j, u, x, and z is independently an integer having a value of 0 to 70. In an even further aspect, each of j, u, x, and z is independently an integer having a value of 0 to 60. In a still further aspect, each of j, u, x, and z is independently an integer having a value of 0 to 50. In a yet further aspect, each of j, u, x, and z is independently an integer having a value of 0 to 40. In an even further aspect, each of j, u, x, and z is independently an integer having a value of 0 to 30. In a still further aspect, each of j, u, x, and z is independently an integer having a value of 0 to 20. In a yet further aspect, each of j, u, x, and z is independently an integer having a value of 0 to 10.

In a further aspect, each of j, u, x, and z is independently an integer having a value of 1 to 15. In a still further aspect, each of j, u, x, and z is independently an integer having a value of 2 to 15. In a yet further aspect, each of j, u, x, and z is independently an integer having a value of 3 to 15. In an even further aspect, each of j, u, x, and z is independently an integer having a value of 4 to 15. In a still further aspect, each of j, u, x, and z is independently an integer having a value of 5 to 15. In a yet further aspect, each of j, u, x, and z is independently an integer having a value of 6 to 15. In an even further aspect, each of j, u, x, and z is independently an integer having a value of 7 to 15. In a still further aspect, each of j, u, x, and z is independently an integer having a value of 8 to 15. In a yet further aspect, each of j, u, x, and z is independently an integer having a value of 9 to 15. In an even further aspect, each of j, u, x, and z is independently an integer having a value of 10 to 15.

In a one aspect, the invention relates to a compound having the structure represented by a formula:

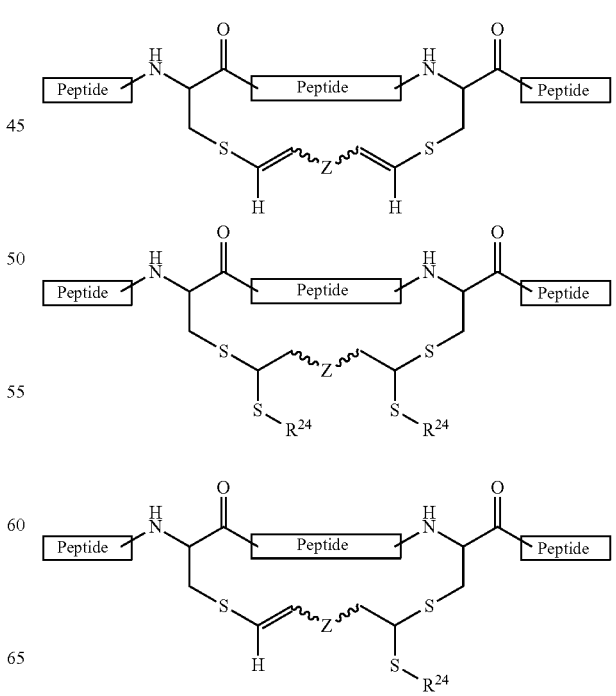

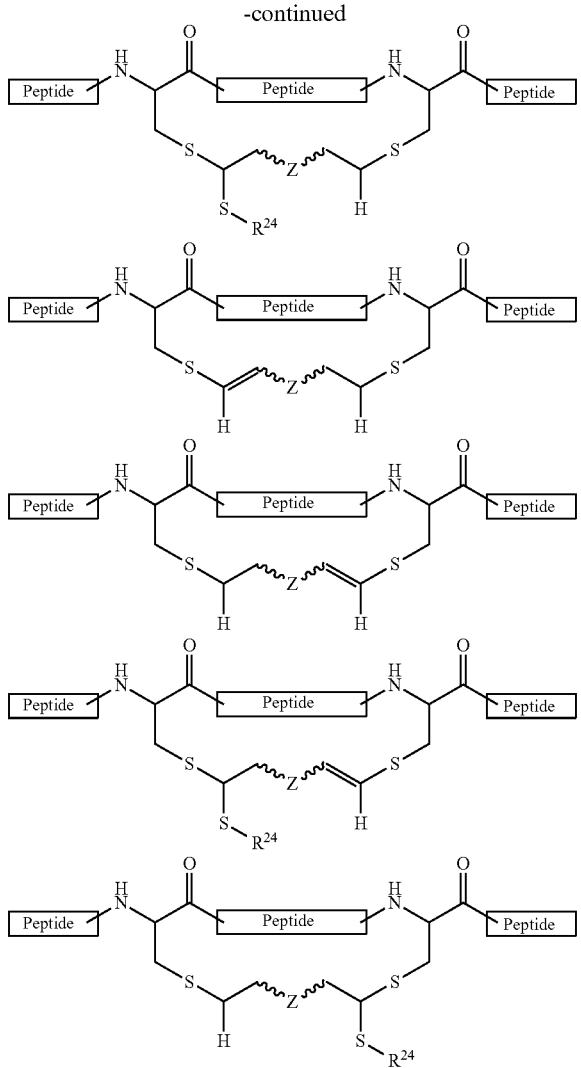

wherein "peptide" represents one or more amino acid residues.

In various aspects, the invention relates to a peptide prepared by any of the disclosed methods. In a further aspect, the invention relates to a stapled peptide prepared by a disclosed method, wherein the peptide has the sequence:

```
HSQGTFTSDYSKYLDSCRAQCFVQWLMNT,   (SEQ ID NO: 1)

HSQGTFTSDYSKYLDSRRACDFVCWLMNT,   (SEQ ID NO: 2)

HSQGTFTSDYSKYLDSRRACDFVQWLCNT,   (SEQ ID NO: 3)

HSQGTFTSDYSKYLDSRRAQCFVQWLMCT,   (SEQ ID NO: 4)
or

HSQGTFTSDYSKYLDSRRAQDFVCWLMCT.   (SEQ ID NO: 5)
```

In a further aspect, the invention relates to a stapled peptide prepared by a disclosed method, wherein the peptide has the sequence:

```
HSQGTFTSDYSKYLDSCRAQCFVQWLMNT,   (SEQ ID NO: 1)

HSQGTFTSDYSKYLDSRRACDFVCWLMNT,   (SEQ ID NO: 2)

HSQGTFTSDYSKYLDSRRACDFVQWLCNT,   (SEQ ID NO: 3)

HSQGTFTSDYSKYLDSRRAQCFVQWLMCT,   (SEQ ID NO: 4)
or

HSQGTFTSDYSKYLDSRRAQDFVCWLMCT;   (SEQ ID NO: 5)
``` and wherein reacting comprises reacting in the presence of a radical initiator.

a. $[X_{AA}]_X$ Groups

In various aspects, each instance of $X_{aa}$ in $[X_{aa}]_x$ is, independently, a natural or unnatural amino acid residue when x is 1 to 100; and $[X_{aa}]_x$ is hydrogen when x is 0.

In a further aspect, x is not 0, and each instance of $X_a$ in $[X_{aa}]_x$ is, independently, a natural or unnatural amino acid residue.

In a further aspect, x is 0 and $[X_{aa}]_x$ is hydrogen.

In various aspects, each instance of $X_{aa}$ in $[X_{aa}]_x$ is, independently, a natural amino acid residue when x is 1 to 100; and $[X_{aa}]_x$ is hydrogen when x is 0.

In a further aspect, x is not 0, and each instance of $X_a$ in $[X_{aa}]_x$ is, independently, a natural amino acid residue.

b. $[X_{AA}]_Y$ Groups

In various aspects, each instance of $X_{aa}$ in $[X_{aa}]_y$ is, independently, a natural or unnatural amino acid.

In a further aspect, each instance of $X_{aa}$ in $[X_{aa}]_y$ is, independently, a natural amino acid.

c. $[X_{AA}]_Z$ Groups

In various aspects, each instance of $X_{aa}$ in $[X_{aa}]$ is, independently, a natural or unnatural amino acid when z is 1 to 100; and wherein $[X_{aa}]_z$ is hydroxy when z is 0.

In a further aspect, z is not 0, and each instance of $X_{aa}$ in $[X_{aa}]_z$ is, independently, a natural or unnatural amino acid residue.

In a further aspect, z is 0 and $[X_{aa}]_z$ is hydroxy.

In various aspects, each instance of $X_{aa}$ in $[X_{aa}]$ is, independently, a natural amino acid residue when z is 1 to 100; and $[X_{aa}]_z$ is hydrogen when x is 0.

In a further aspect, z is not 0, and each instance of $X_{aa}$ in $[X_{aa}]_z$ is, independently, a natural amino acid residue.

d. $R^{1A}$ and $R^{1B}$ Groups

In one aspect, each of $R^{1a}$ and $R^{1b}$ is independently hydrogen or an amino protecting group. In a further aspect, each of $R^{1a}$ and $R^{1b}$ is hydrogen.

In a further aspect, each of $R^{1a}$ and $R^{1b}$ is an amino protecting group. In a still further aspect, each of $R^{1a}$ and $R^{1b}$ is an amino protecting group, and the amino protecting group is a Fmoc protecting group. In a yet further aspect, each of $R^{1a}$ and $R^{1b}$ is an amino protecting group, and the amino protecting group is a Boc protecting group.

e. $R^{2A}$ and $R^{2B}$ Groups

In one aspect, each of $R^{2a}$ and $R^{2b}$ is independently hydrogen or C1-C4 alkyl. In a further aspect, each of $R^{2a}$ and $R^{2b}$ is hydrogen. In a still further aspect, each of $R^{2a}$ and $R^{2b}$ is methyl.

In a further aspect, each of $R^{2a}$ and $R^{2b}$ is independently hydrogen, methyl, ethyl, propyl, or isopropyl. In a still further aspect, each of $R^{2a}$ and $R^{2b}$ is independently hydrogen, methyl, or ethyl. In a yet further aspect, each of $R^{2a}$ and $R^{2b}$ is independently hydrogen or methyl. In an even further aspect, each of $R^{2a}$ and $R^{2b}$ is independently hydrogen or ethyl. In a still further aspect, each of $R^{2a}$ and $R^{2b}$ is independently hydrogen, propyl, or isopropyl.

f. $R^{3A}$ and $R^{3B}$ Groups

In one aspect, each of $R^{3a}$ and $R^{3b}$ is independently a C1-C4 alkylene.

In a further aspect, wherein each of $R^{3a}$ and $R^{3b}$ is independently —$CH_2$— or —$(CH_2)_2$—. In a still further aspect, each of $R^{3a}$ and $R^{3b}$ is —$CH_2$—. In a yet further aspect, each of $R^{3a}$ and $R^{3b}$ is —$(CH_2)_2$—.

g. $R^{4A}$, $R^{4B}$, $R^{4C}$, and $R^{4D}$ Groups

In one aspect, each of $R^{4a}$, $R^{4b}$, $R^{4c}$, and $R^{4d}$ is independently hydrogen, hydroxy, amino, C1-C4 alkyl, and —$CO_2H$. In a further aspect, each of $R^{4a}$, $R^{4b}$, $R^{4c}$, and $R^{4d}$ is hydrogen.

In a further aspect, each of $R^{4a}$, $R^{4b}$, $R^{4c}$, and $R^{4d}$ is hydrogen, hydroxy, amino, or C1-C4 alkyl. In a still further aspect, each of $R^{4a}$, $R^{4b}$, $R^{4c}$, and $R^{4d}$ is hydrogen, hydroxy, amino, methyl, ethyl, propyl, or isopropyl. In a yet further aspect, each of $R^{4a}$, $R^{4b}$, $R^{4c}$, and $R^{4d}$ is hydrogen, hydroxy, amino, methyl, or ethyl. In an even further aspect. In a still further aspect, each of $R^{4a}$, $R^{4b}$, $R^{4c}$, and $R^{4d}$ is hydrogen, hydroxy, amino, or methyl.

In a further aspect, each of $R^{4a}$, $R^{4b}$, $R^{4c}$, and $R^{4d}$ is hydrogen or C1-C4 alkyl. In a still further aspect, each of $R^{4a}$, $R^{4b}$, $R^{4c}$, and $R^{4d}$ is hydrogen, methyl, ethyl, propyl, or isopropyl. In a yet further aspect, each of $R^{4a}$, $R^{4b}$, $R^{4c}$, and $R^{4d}$ is hydrogen, methyl, or ethyl. In an even further aspect. In a still further aspect, each of $R^{4a}$, $R^{4b}$, $R^{4c}$, and $R^{4d}$ is hydrogen or methyl.

In a further aspect, each of $R^{4a}$, $R^{4b}$, $R^{4c}$, and $R^{4d}$ is hydrogen, hydroxy, or amino. In a still further aspect, each of $R^{4a}$, $R^{4b}$, and $R^{4c}$ is hydrogen, and $R^{4d}$ is hydroxy or amino. In a yet further aspect, each of $R^{4a}$, $R^{4b}$, and $R^{4d}$ is hydrogen, and $R^{4c}$ is hydroxy or amino. In an even further aspect, each of $R^{4a}$, $R^{4c}$, and $R^{4d}$ is hydrogen, and $R^{4b}$ is hydroxy or amino. In a still further aspect, each of $R^{4b}$, $R^{4c}$, and $R^{4d}$ is hydrogen, and $R^{4a}$ is hydroxy or amino.

In a further aspect, a still further aspect, each of $R^{4a}$, $R^{4b}$, and $R^{4c}$ is hydrogen, and $R^{4d}$ is —$CO_2H$. In a yet further aspect, each of $R^{4a}$, $R^{4b}$, and $R^{4d}$ is hydrogen, and $R^{4c}$ is —$CO_2Ho$. In an even further aspect, each of $R^{4a}$, $R^{4c}$, and $R^{4d}$ is hydrogen, and $R^{4b}$ is —$CO_2H$. In a still further aspect, each of $R^{4b}$, $R^{4c}$, and $R^{4d}$ is hydrogen, and $R^{4a}$ is —$CO_2H$.

h. $R^{11}$ and $R^{12}$ Groups

In one aspect, each of $R^{11}$ and $R^{12}$ is independently C3-C6 alkylene.

In a further aspect, wherein each of $R^{11}$ and $R^{12}$ is independently —$(CH_2)_3$—, —$(CH_2)_4$—, or —$(CH_2)_5$—. In a still further aspect, each of $R^{11}$ and $R^{12}$ is —$(CH_2)_3$—. In a still further aspect, each of $R^{11}$ and $R^{12}$ is —$(CH_2)_4$—. In a still further aspect, each of $R^{11}$ and $R^{12}$ is —$(CH_2)_5$—. In a still further aspect, each of $R^{11}$ and $R^{12}$ is —$(CH_2)_6$—.

i. Z Groups

In one aspect, Z is C5-C12 alkylene, —(C2-C6 alkylene)-O—(C2-C6 alkylene)-, —$(CH_2)_3$—$(OCH_2CH_2)_q$—O—$(CH_2)_3$—, or a moiety represented by a formula:

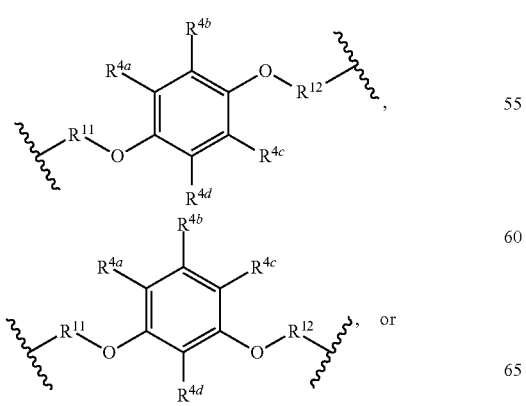

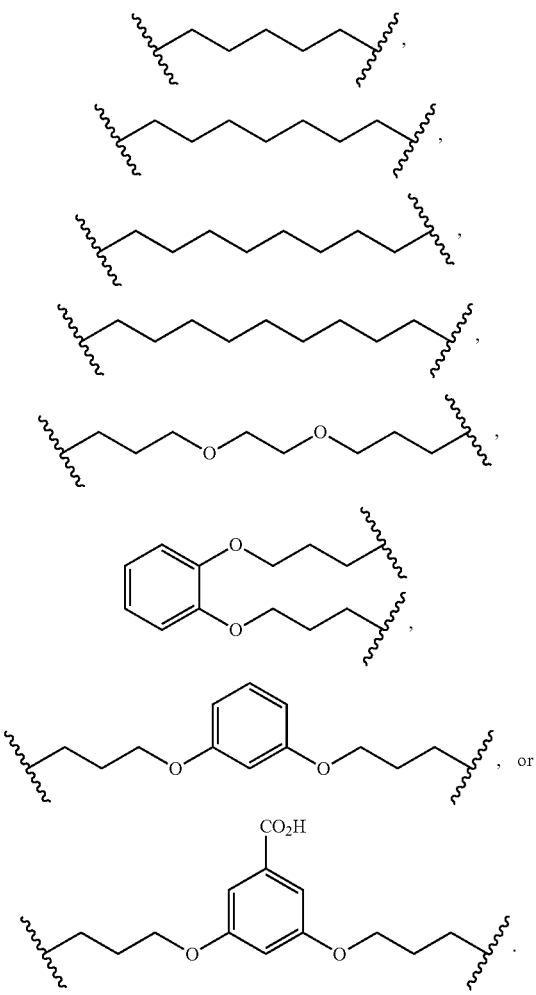

In a further aspect, Z is a moiety represented by a formula:

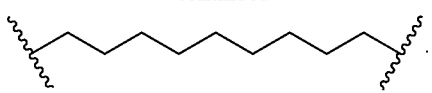

In a further aspect, Z is a moiety represented by a formula:

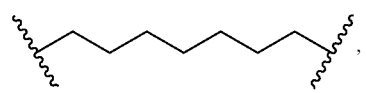,

, or

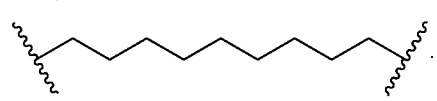.

In a further aspect, Z is a moiety represented by a formula:

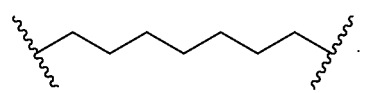 [SMILES: *CCCCCCC*].

In a further aspect, Z is a moiety represented by a formula:

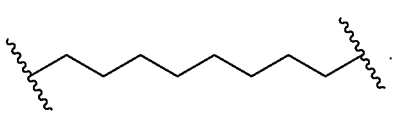 [SMILES: *CCCCCCCC*].

In a further aspect, Z is a moiety represented by a formula:

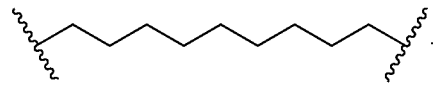 [SMILES: *CCCCCCCCC*].

In a further aspect, Z is a moiety represented by a formula:

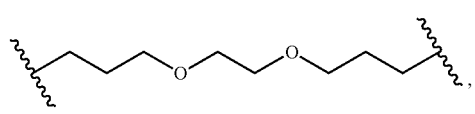,

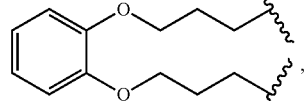,

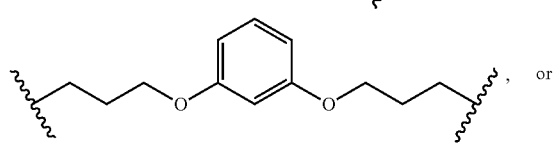, or

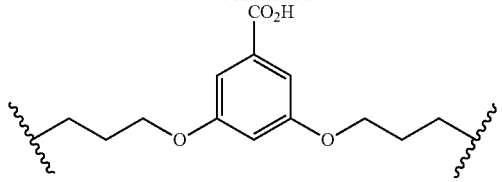.

In a further aspect, Z is a moiety represented by a formula:

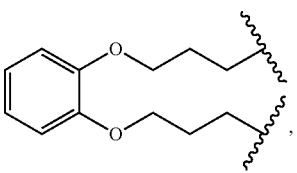,

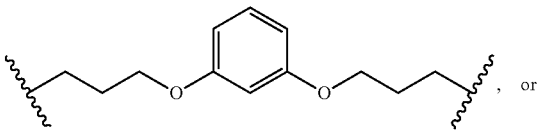, or

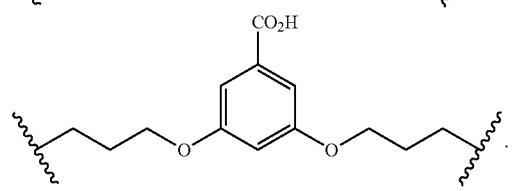.

In a further aspect, Z is a moiety represented by a formula:

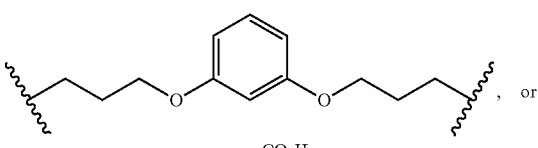, or

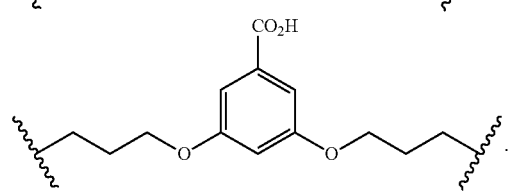.

In a further aspect, Z is a moiety represented by a formula:

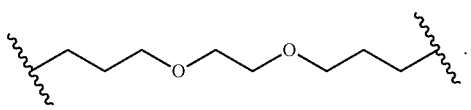 [SMILES: *CCCOCCOCCC*].

In a further aspect, Z is a moiety represented by a formula:

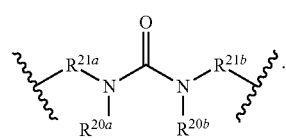.

In a further aspect, the linker can be a residue of a bifunctional Michel Acceptor. For example, Z can be a moiety represented by a formula:

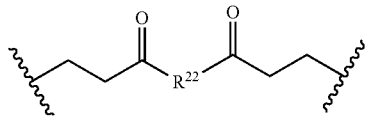

wherein $R^{22}$ is an alkylene moiety having from 1 to 12 carbons, e.g., C1-C8, C1-C6, C1-C4, or C1-C2.

As would be appreciated by those of skill, a bifunctional Michael Acceptor can have a structure, e.g., represented by a formula:

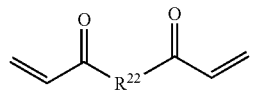

wherein $R^{22}$ is an alkylene moiety having from 1 to 12 carbons, e.g., C1-C8, C1-C6, C1-C4, or C1-C2.

j. $R^{20}$ Groups

In one aspect, each of $R^{20a}$ and $R^{20b}$ is independently selected from hydrogen and C1-C4 alkyl (e.g., methyl, ethyl, propyl, or butyl). For example, $R^{20a}$ can be hydrogen. As a further example, $R^{20a}$ can be C1-C4 alkyl, C1-C3 alkyl, C1-C2 alkyl, methyl, ethyl, propyl, or butyl. For example, $R^{20b}$ can be hydrogen. As a further example, $R^{20b}$ can be C1-C4 alkyl, C1-C3 alkyl, C1-C2 alkyl, methyl, ethyl, propyl, or butyl.

k. $R^{21}$ Groups

In one aspect, each of $R^{21a}$ and $R^{21b}$ is independently C3-C6 alkylene (e.g., methylene, ethylene, or propylene). For example, $R^{21a}$ can be methylene, ethylene, or propylene. For example, $R^{21b}$ can be methylene, ethylene, or propylene.

l. $R^{22}$ Groups

In one aspect, $R^{22}$ is selected from: hydrogen when adjacent a double bond and hydrogen or —$SR^{24}$ when adjacent a single bond, provided that both $R^{22}$ and $R^{23}$ are not simultaneously hydrogen adjacent a single bond. For example, $R^{22}$ can be hydrogen and adjacent a double bond. As a further example, $R^{22}$ can be hydrogen and adjacent a single bond. As a further example, $R^{22}$ can be —$SR^{24}$ and adjacent a single bond.

Said another way, the disclosed compounds can, in various aspects, comprise the below moieties:

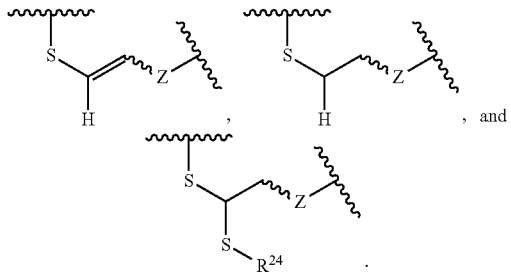

m. $R^{23}$ Groups

In one aspect, $R^{23}$ is selected from: hydrogen when adjacent a double bond and hydrogen or —$SR^{24}$ when adjacent a single bond, provided that both $R^{22}$ and $R^{23}$ are not simultaneously hydrogen adjacent a single bond. For example, $R^{23}$ can be hydrogen and adjacent a double bond. As a further example, $R^{23}$ can be hydrogen and adjacent a single bond. As a further example, $R^{23}$ can be —$SR^{24}$ and adjacent a single bond.

Said another way, the disclosed compounds can, in various aspects, comprise the below moieties:

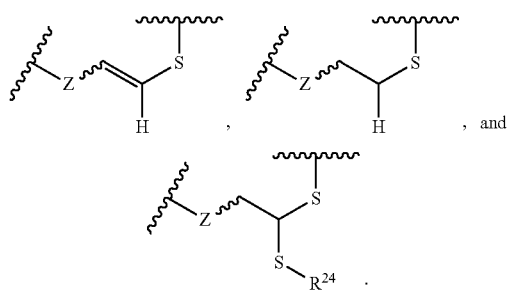

In further examples, $R^{22}$ and $R^{23}$ can, in various aspects, be selected to provide the following staple structures:

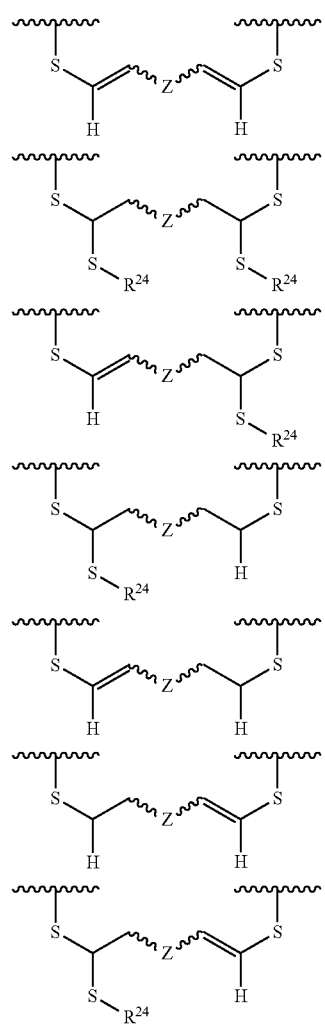

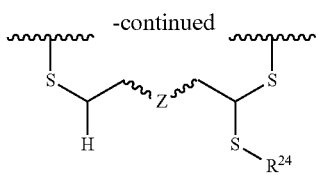

n. $R^{24}$ Groups

In one aspect, each $R^{24}$, when present, is independently selected from hydrogen, C1-C24 alkyl, $—(CH_2CH_2O)_n(C1$-C4 alkyl), a solubilizing functionality, a labeling functionality, a tether to solid-phase support, or a tether to a second peptide.

In a further aspect, C1-C24 alkyl includes C1-C4 alkyl, C1-C4 alkyl, C1-C6 alkyl, C1-C6 alkyl, C1-C8 alkyl, C1-C8 alkyl, C1-C10 alkyl, C1-C10 alkyl, C1-C12 alkyl, C1-C12 alkyl, C1-C16 alkyl, C1-C16 alkyl, C1-C20 alkyl, C1-C20 alkyl, and C2-C24 alkyl. For example, $R^{24}$ can be any of methyl, ethyl, propyl, butyl, pentyl, hexyl, heptyl, octyl, nonyl, decyl, undecyl, and docecyl, as well as groupings thereof.

In a further aspect, $R^{24}$ can be $—(CH_2CH_2O)_n(C1$-C4 alkyl), wherein each occurrence of n is an integer from 1-12 (e.g., 1-2, 1-3, 1-4, 1-6, 1-8, 1-10, 2-3, 2-4, 2-6, 2-8, or 2-10). In further aspects, $—(CH_2CH_2O)_n(C1$-C4 alkyl) includes $—(CH_2CH_2O)_n$(methyl), $—(CH_2CH_2O)_n$(ethyl), $—(CH_2CH_2O)_n$(propyl), and $—(CH_2CH_2O)_n$(butyl).

In certain aspects, solubilizing functionalities useful in connection with the disclosed compounds and methods include poly-arginines.

In certain aspects, labeling functionalities useful in connection with the disclosed compounds and methods include fluorophores.

In certain aspects, tethers to solid-phase support useful in connection with the disclosed compounds and methods include agarose beads.

In certain aspects, tethers to a second peptide useful in connection with the disclosed compounds and methods include cell-penetrating peptides and tissue-targeting peptides.

2. Example Peptides

In one aspect, a stapled peptide can be present as:

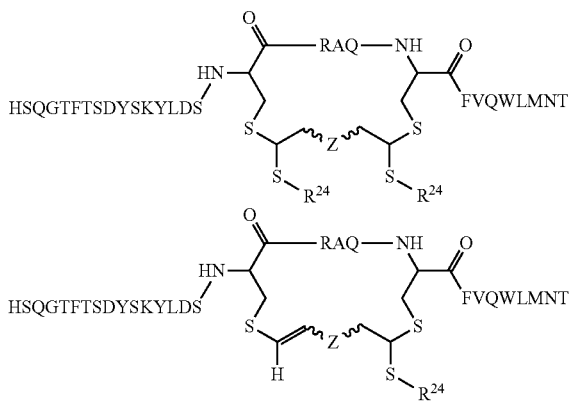

In one aspect, a stapled peptide can be present as:

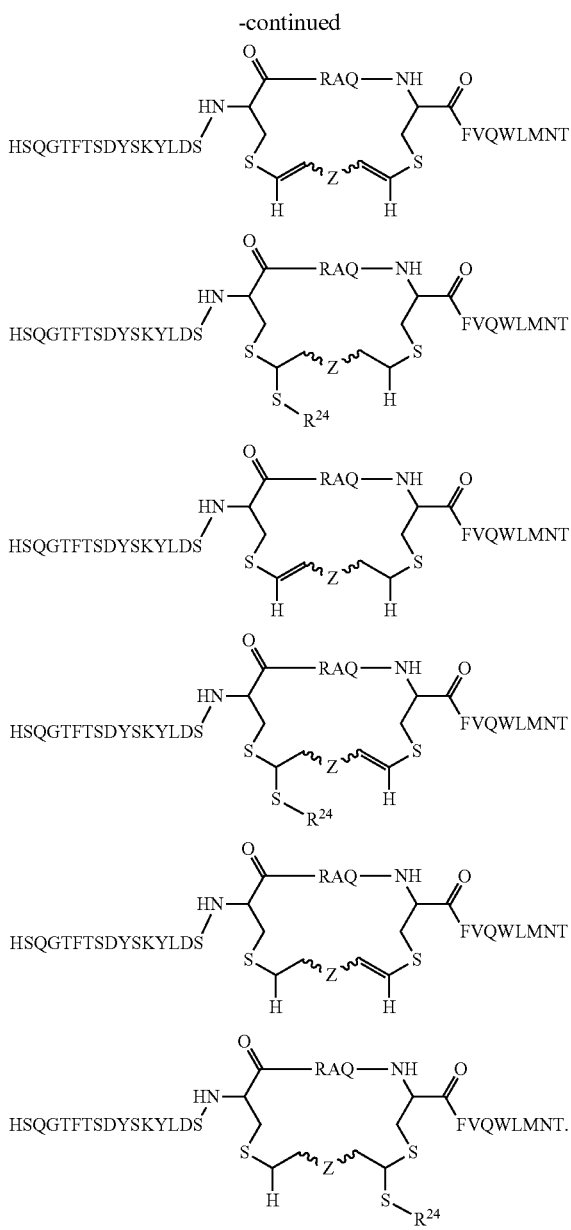

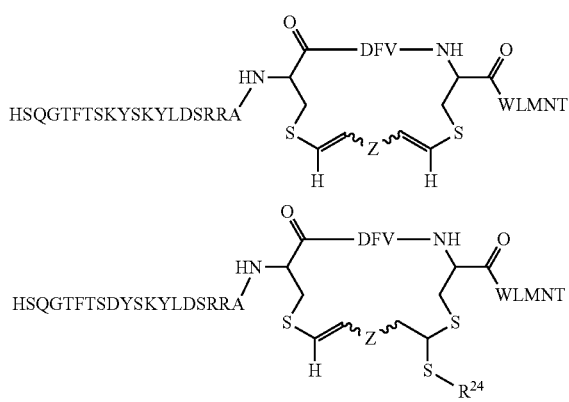

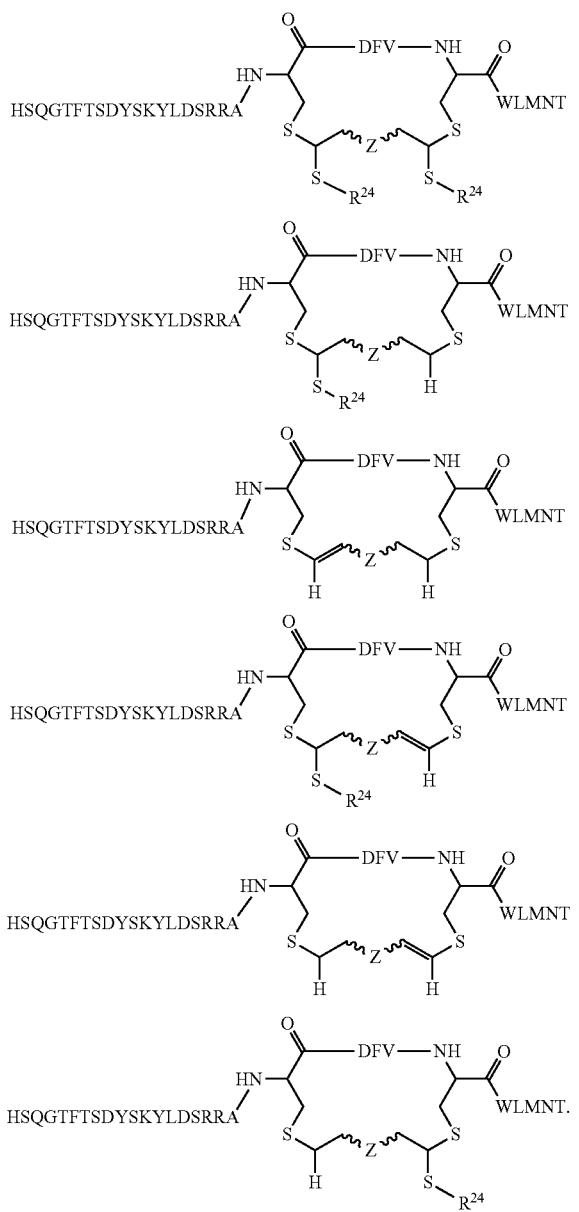
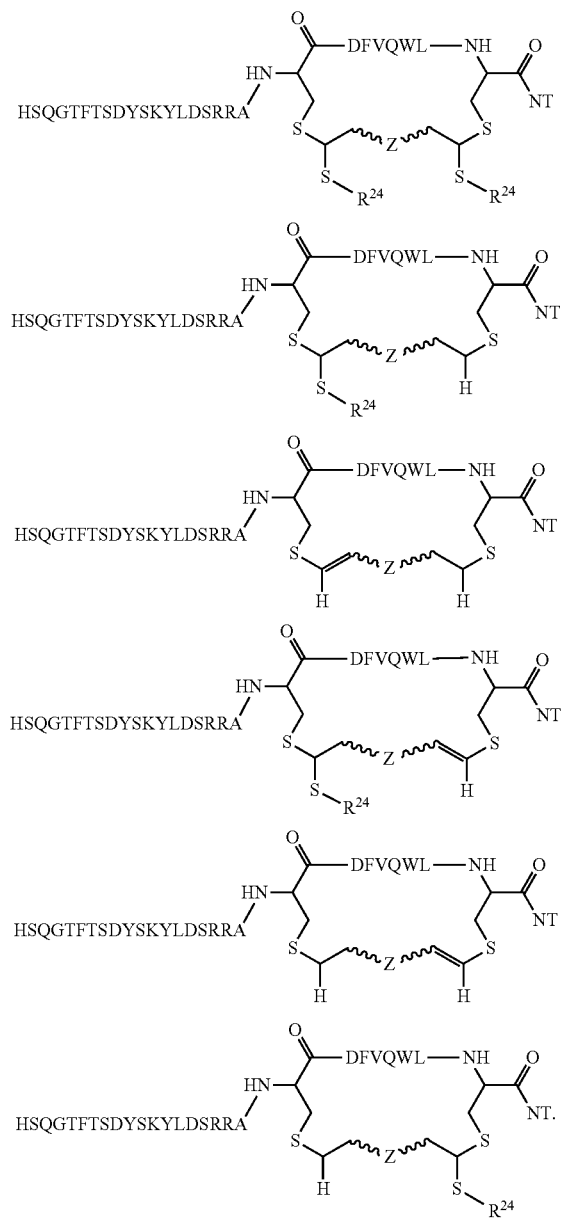
In one aspect, a stapled peptide can be present as:
In one aspect, a stapled peptide can be present as:
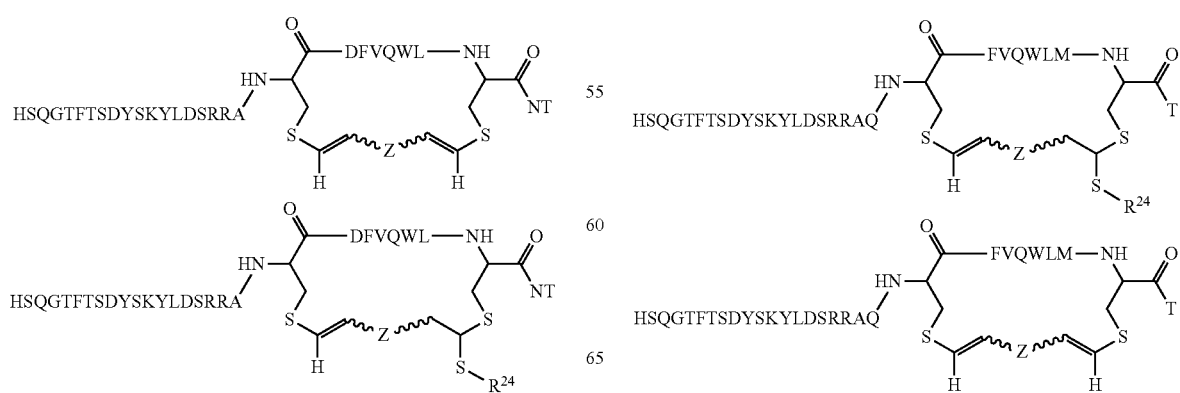

-continued

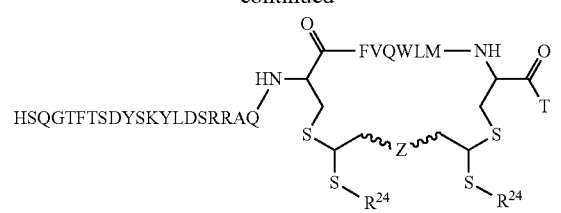
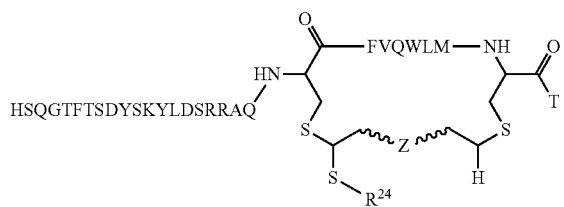
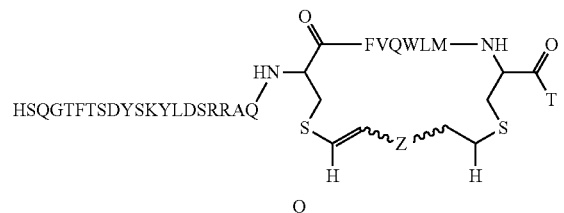
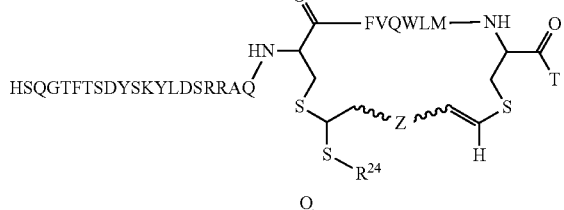
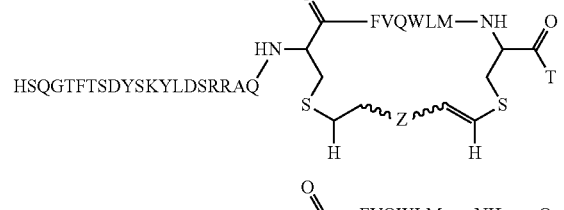
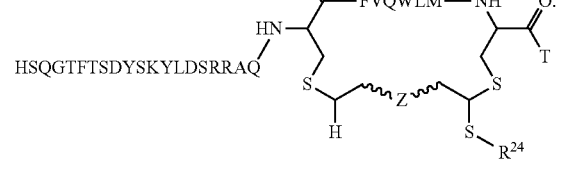

In one aspect, a stapled peptide can be present as:

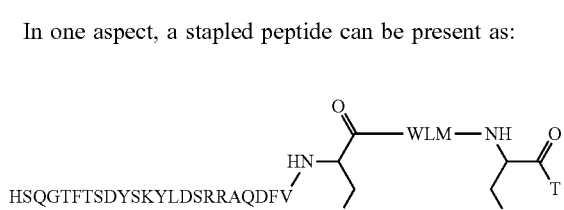
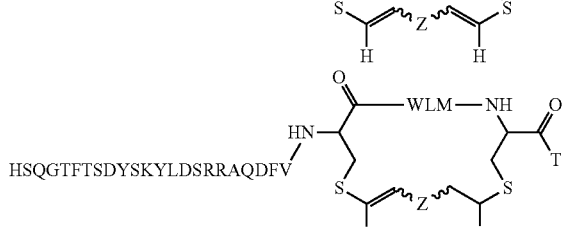

-continued

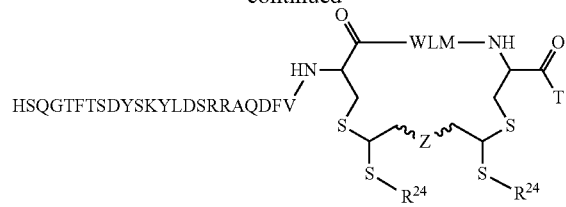
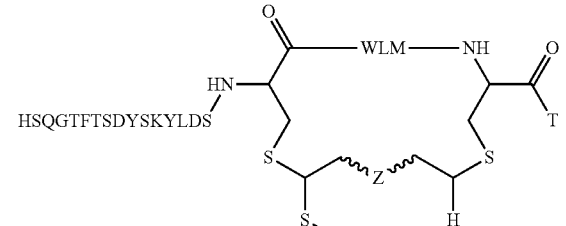
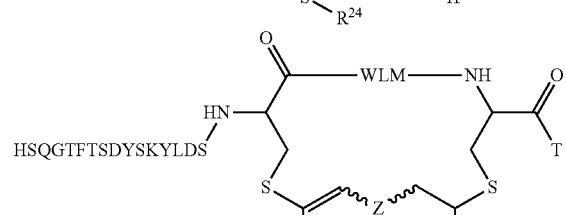
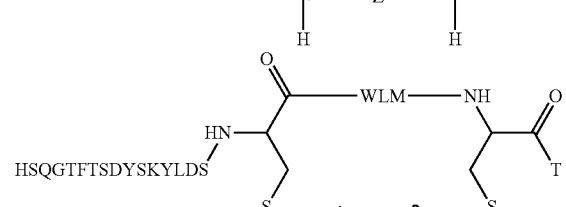
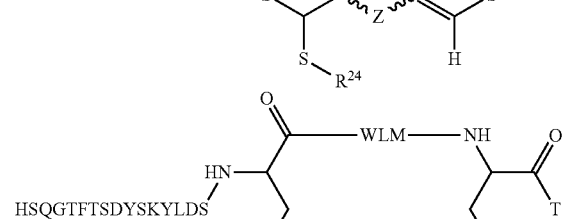
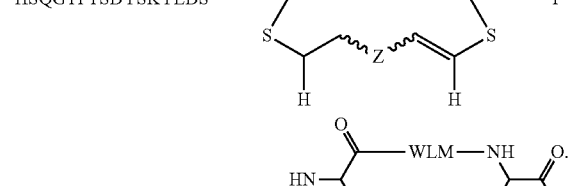
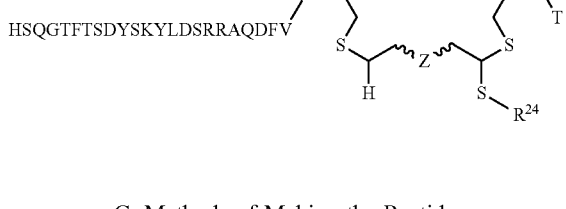
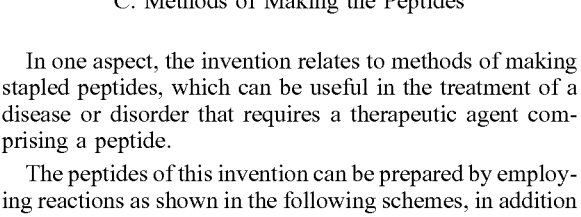

C. Methods of Making the Peptides

In one aspect, the invention relates to methods of making stapled peptides, which can be useful in the treatment of a disease or disorder that requires a therapeutic agent comprising a peptide.

The peptides of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the peptides of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In various aspects, the invention relates to methods of stapling a peptide having two thiol functionalities with a linker having two alkene functionalities, the method comprising the step of reacting the two thiol functionalities with the two alkene functionalities. In a further aspect, the two thiol functionalities are contained in two cysteine residues in the peptide. In a further aspect, the peptide contains all natural residues. In a further aspect, the reaction is a free-radical reaction. In a further aspect, the reaction is a Michael addition. In a further aspect, the method further comprises a second reaction between two further thiol functionalities in the peptide and two further alkene functionalities in a further linker.

In various aspects, the invention relates to methods of preparing a stapled peptide, the method comprising reacting a bis-terminal diene with a peptide comprising a first amino acid residue with a thiol-containing R group and a second amino acid residue with a thiol-containing R group.

In a further aspect, the reacting further comprises reacting with a radical initiator. In a still further aspect, the radical initiator is a photoinitiator. In a yet further aspect, the photoinitiator is 2,2-dimethoxy-2-phenylacetophenone, 9,10-dioxo-9,10-dihydroanthracene-2-sulfonic acid, or (phenylphosphoryl)bis(mesitylmethanone). In an even further aspect, the photoinitiator is 2,2-dimethoxy-2-phenylacetophenone. In a still further aspect, the photoinitiator is 9,10-dioxo-9,10-dihydroanthracene-2-sulfonic acid. In an even further aspect, the photoinitiator is (phenylphosphoryl) bis(mesitylmethanone).

In a further aspect, the peptide has the sequence:

```
HSQGTFTSDYSKYLDSCRAQCFVQWLMNT,  (SEQ ID NO: 1)

HSQGTFTSDYSKYLDSRRACDFVCWLMNT,  (SEQ ID NO: 2)

HSQGTFTSDYSKYLDSRRACDFVQWLCNT,  (SEQ ID NO: 3)

HSQGTFTSDYSKYLDSRRAQCFVQWLMCT,  (SEQ ID NO: 4)
or

HSQGTFTSDYSKYLDSRRAQDFVCWLMCT.  (SEQ ID NO: 5)
```

In one aspect, the disclosed peptides comprise the products of the synthetic methods described herein. In a further aspect, the disclosed peptides comprise a peptide produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one peptide of any of disclosed peptides or at least one product of the disclosed methods with a pharmaceutically acceptable carrier or diluent. In a further aspect, the method further comprises a further reaction between two further thiol functionalities in the peptide and two further unsaturated functionalities in a further linker.

In one aspect, the invention relates to a method of stapling a peptide having two thiol functionalities with a linker having two unsaturated functionalities comprising two alkyne moieties or comprising one alkyne moiety and one alkene moiety, the method comprising a first reacting step of the two thiol functionalities with the two unsaturated functionalities, thereby providing two alkenyl sulfide moieties or thereby providing one alkenyl sulfide moiety and one alkyl sulfide moiety, and optionally, a second reacting step of the one or two alkenyl sulfide moieties with one or two radical agents or one or two nucleophilic agents.

In a further aspect, the two thiol functionalities are contained in two cysteine residues in the peptide. In a further aspect, the peptide contains all natural residues.

In a further aspect, the first reacting step is a free-radical reaction. In a further aspect, the first reacting step is a Michael addition. In a further aspect, the second reacting step is a free-radical reaction. In a further aspect, the second reacting step is a Michael addition.

In a further aspect, the method further comprises the second reacting step of the two alkenyl sulfide moieties with two radical agents or two nucleophilic agents. In a further aspect, the two alkenyl sulfide moieties are reacted with two radical agents. In a further aspect, the two radical agents comprise thiols. In a further aspect, one or more of the two radical agents comprise a solubilizing functionality, a labeling functionality, a tether to solid-phase support, or a thether to a second peptide. In a further aspect, the two alkenyl sulfide moieties are reacted with two nucleophilic agents. In a further aspect, the two nucleophilic agents comprise alcohols and/or amines, and wherein the two alkenyl sulfide moieties comprise Michael acceptors. In a further aspect, one or more of the two nucleophilic agents comprises a solubilizing functionality, a labeling functionality, a tether to solid-phase support, or a tether to a second peptide.

In a further aspect, the method further comprises the second reacting step of the one alkenyl sulfide moiety with one radical agent or one nucleophilic agent. In a further aspect, the alkenyl sulfide moiety is reacted with a radical agent. In a further aspect, the radical agent comprises a thiol. In a further aspect, the radical agent comprises a solubilizing functionality, a labeling functionality, a tether to solid-phase support, or a thether to a second peptide. In a further aspect, the alkenyl sulfide moiety is reacted with a nucleophilic agent. In a further aspect, the nucleophilic agent comprises an alcohol or an amine, and wherein the alkenyl sulfide moiety comprises a Michael acceptor. In a further aspect, the nucleophilic agent comprises a solubilizing functionality, a labeling functionality, a tether to solid-phase support, or a tether to a second peptide.

In a further aspect, the linker has two alkyne moieties, the first reacting step thereby providing two alkenyl sulfide moieties, and wherein the a second reacting step is performed with two thiols. In a further aspect, each of the two thiols independently comprises a solubilizing functionality, a labeling functionality, a tether to solid-phase support, or a thether to a second peptide.

In one aspect, the invention relates to a method of preparing a stapled peptide, the method comprising reacting a bis-terminal diyne with a peptide comprising a first amino acid residue with a thiol-containing R group and a second amino acid residue with a thiol-containing R group. In a further aspect, the peptide has the sequence

HSQGTFTSDYSKYLDSCRAQCFVQWLMNT,  (SEQ ID NO: 1)

HSQGTFTSDYSKYLDSRRACDFVCWLMNT,  (SEQ ID NO: 2)

HSQGTFTSDYSKYLDSRRACDFVQWLCNT,  (SEQ ID NO: 3)

HSQGTFTSDYSKYLDSRRAQCFVQWLMCT,  (SEQ ID NO: 4)
or

HSQGTFTSDYSKYLDSRRAQDFVCWLMCT.  (SEQ ID NO: 5)

In one aspect, the invention relates to a method of preparing a stapled peptide, the method comprising the steps of: providing a peptide having the structure represented by the formula:

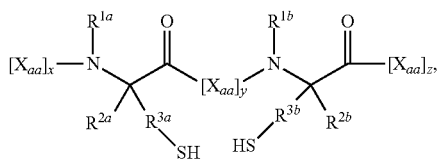

wherein each of x and z is independently an integer having a value of 0 to 100; wherein y is an integer having a value of 1 to 20; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a linker compound having the structure represented by the formula:

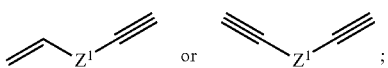

wherein $Z^1$ is C1-C8 alkyl, C3-C8 ether, C6-C8 polyether, or a moiety represented by a formula:

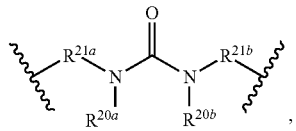

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

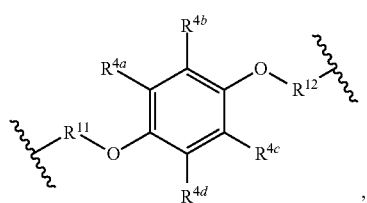

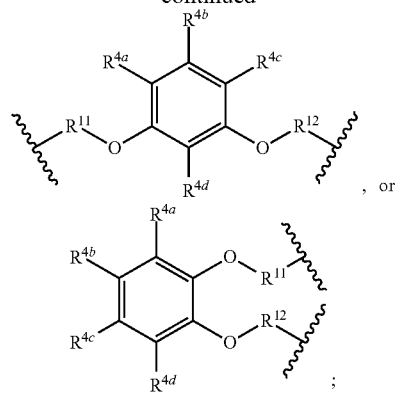

wherein each of $R^{4a}$, $R^{4b}$, $R^{4c}$, and $R^{4d}$ is independently hydrogen, hydroxy, amino, C1-C4 alkyl, and $—CO_2H$; and wherein each of $R^{13}$ and $R^{14}$ is independently C1-C4 alkyl; reacting the peptide and the linker compound; thereby forming the stapled peptide. In a further aspect, the reaction is performed in the presence of a radical initiator.

In one aspect, the invention relates to a method of preparing a stapled peptide, the method comprising the steps of: providing a first peptide and a second peptide having, respectively, the structure represented by the formulas:

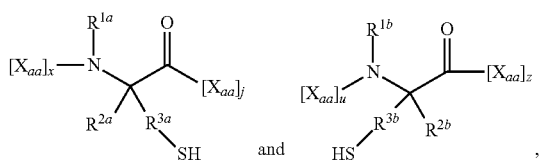

wherein each of j, u, x, and z is independently an integer having a value of 0 to 100; provided that j and x are not simultaneously 0; and provided that u and z are not simultaneously 0; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a linker compound having the structure represented by the formula:

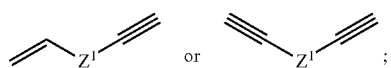

wherein $Z^1$ is C1-C8 alkyl, C3-C8 ether, C6-C8 polyether, or a moiety represented by a formula:

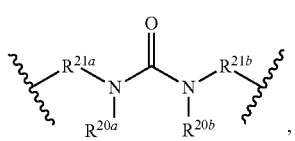

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

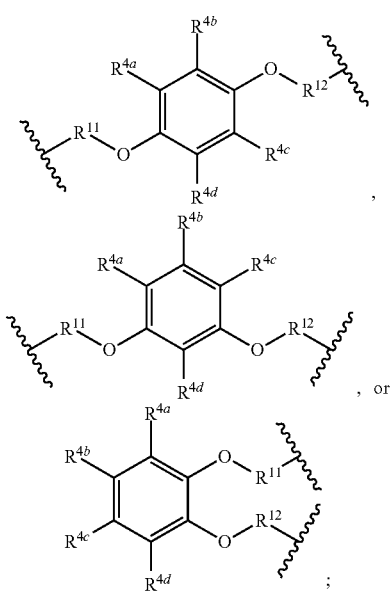

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; reacting the peptide and the linker compound; thereby forming the stapled peptide. In a further aspect, the reaction is performed in the presence of a radical initiator.

D. Pharmaceutical Compositions

In one aspect, the invention relates to pharmaceutical compositions comprising the disclosed peptides. That is, a pharmaceutical composition can be provided comprising a therapeutically effective amount of at least one disclosed peptide or at least one product of a disclosed method and a pharmaceutically acceptable carrier.

In certain aspects, the disclosed pharmaceutical compositions comprise the disclosed peptides (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a peptide of the invention, and/or pharmaceutically acceptable salts thereof, can also be prepared in powder or liquid concentrate form.

In the treatment conditions which require modulation of a therapeutic target by a disclosed peptide, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the peptides of this invention are illustrated in the following Examples. Starting materials and the requisite intermediates are in some cases commercially available, or can be prepared according to literature procedures or as illustrated herein.

1. Chemicals and Abbreviations 1,4-Pentadiene, 1,6-heptadiene, 1,7-octadiene, 1,8-nonadiene, N-Acetyl-L-cysteine methyl ester, 2,2-dimethoxy-2-phenyl-acetophenone, piperidine, triisopropylsilane (TIS), 1.2-ethanedithiol (EDT) and reduced L-glutathione, azobisisobutyronitrile, anthraquinone-2-sulfonic acid sodium, 1,2-bis(4,5-dihydro-1H-imidazol-2-yl)propan-2-yl)diazene dihydrochloride, phenylbis(2,4,6-trimethylbenzoyl)phosphine oxide were purchased from Sigma-Aldrich. Dithiothreitol (DTT) and tris(2-carboxyethyl)phosphine hydrochloride (TCEP) were purchased from Gold Bio Technology. (R)—N-Fmoc-2-(7'-octenyl)alanine and (S)—N-Fmoc-2-(4'-pentenyl)alanine were provided by Okeanos Tech Jiangsu Co. Ltd. Fmoc-protected amino acids were obtained from Protein technologies Inc. O-(Benzotriazol-1-yl)-N,N,N',N'-tetramethyluronium (HBTU) and 1-[Bis(dimethylamino)methylene]-1H-1,2,3-triazolo[4,5-b]pyridinium 3-oxid hexafluorophosphate (HATU) were purchased from ChemPep. Rink Amide MBHA resin HL was obtained from Novabiochem and H-Rink Amide ChemMatrix was provided by Biotage. Dimethylformamide (DMF), N-methylpyrrolidinone (NMP), trifluoroacetic acid (TFA), acetonitrile and ethyl ether were purchased from Fisher Scientific and used as supplied.

The following radical initiators can be used in the reactions discussed herein and are designated throughout with the compound numbers indicated in Table I, below.

TABLE I

| Name | Structure |
|---|---|
| 2,2-dimethoxy-2-phenyl-acetophenone | 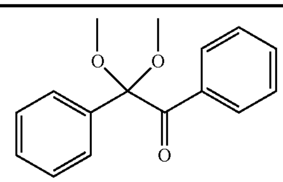 |
| anthraquinone-2-sulfonic acid sodium | 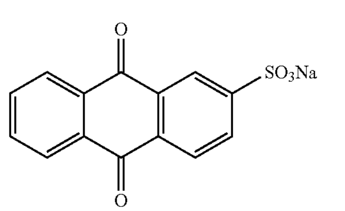 |
| phenylbis(2,4,6-trimethyl-benzoyl)phosphine oxide | |

TABLE I-continued

| Name | Structure |
|---|---|
| azobisisobutyronitrile | 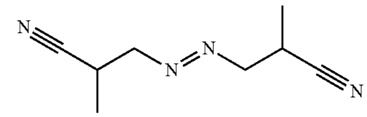 |
| 1,2-bis(4,5-dihydro-1H-imidazol-2-yl)propan-2-yl)diazene dihydrochloride | 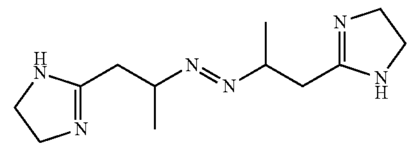 [SMILES: CC(CC1=NCCN1)/N=N/C(C)CC1=NCCN1] |

2. General Methods

Analytical thin layer chromatography (TLC) can be performed on pre-coated silica gel plates available from EMD. Visualization can be accomplished with UV light. Column chromatography can be performed using Biotage chromatographic systems. $^1$H NMR and $^{13}$C NMR spectra can be recorded on Varian Inova instrument (400 MHz). Chemical shifts are quoted in parts per million (ppm) referenced to the residual undeuterated solvent peak or 0.0 ppm for tetramethylsilane. The following abbreviations are used to explain multiplicities: s=singlet, d=doublet, t=triplet, m=multiplet. Coupling constants, J, are reported in Hertz unit (Hz). The yields can be calculated based on the amount of the product after column chromatography using HPLC.

Preparative reverse-phase HPLC of crude peptides can be performed on Luna 5u C8 100 Å (250×10 mm) at 3 mL/min with a water/acetonitrile gradient in 0.1% TFA on an Agilent 1260 HPLC system. Fractions collected from preparative can be analyzed by LC/MS on a XBridge C18 5-μm (50×2.1 mm) column at 0.4 mL/min with a water/acetonitrile gradient in 0.1% formic acid on an Agilent 6120 Quadrupole LC/MS system. Fractions containing targeted product (based on LC/MS) can be collected and lyophilized.

All CD spectra can be recorded on an AVIV Model 410 spectrophotometer (AVIV) in water in a 1 mm QS quartz cuvette (Starna) at 25° C. Wavelength scans can be performed at 1-nm resolution with 1-s averaging time. Data from double scans can be averaged, blank subtracted, and normalized to mean residue ellipticity by the following equation: $[\theta]=100\times\theta/C\times1\times(n-1)$, where C is concentration of protein in mM, 1 is path length in centimeters, and n is the number of residues in the protein. The concentrations of the protein samples used for CD experiments are 100 μM. The percentage helicity can be calculated from the absorbance at 222 nm using helical models as previously reported (Y. H. Chen, J. T. Yang, K. H. Chau. Biochemistry 1974, 13, 3350-3359).

3. Peptide Synthesis.

Peptides can be synthesized via Fmoc solid phase peptide synthesis on a commercial peptide synthesizer (Alstra; Biotage, Inc.). Automated peptide synthesis can be carried out in a 10 mL reactor vial with the following protocols (for 0.1 mmol scale). For Fmoc deprotection: (i) 4.5 mL of 20% piperidine in DMF; (ii) mix 2×3 min (new solvent delivered for each mixing cycle). For amino acid coupling: (i) 1.25 mL of 0.4 M Fmoc-protected amino acid in DMF; (ii) 1.225 mL of 0.4 M HBTU or HATU (HBTU and Rink Amide MBHA resin HL or HATU and H-Rink Amide ChemMatrix can be used for peptides) in DMF; (iii) 1.0 mL of 1.0 M DIPEA in DMF; and (iv) mix for 5 min at 75° C. (for cysteine coupling: mix for 10 min at 50° C.). For DMF washing (performed between deprotection and coupling steps): (i) 4.5 mL of DMF; (ii) mix 45 s. For acetylation at the N-terminus (performed between the last deprotection and precleavage wash with DCM steps): (i) 1.0 mL of 5.0 M acetic anhydride in DMF; (ii) 5.5 mL of 1.0 M DIPEA in DMF; and (iv) mix for 10 min at 25° C. Upon completion of the peptide chain, resins can be washed with DCM and dried (using vacuum) for 20 min. Then peptide can be cleaved from the resin by exposure to cleavage cocktail for 2.5 h, prepared with 12.5 mL TFA, 330 μL water, 330 μL TIS, and 330 μL EDT. The peptide can be precipitated with ethyl ether at 4° C. and lyophilized.

4. Thiol-yne Reaction Between a Peptide and a Diyne

A general reaction schematic is presented in FIG. 1. 1,8-Nonadiyne (1 equiv), DMPA (1 equiv), and NMP were combined. The reaction solution was stirred under UV irradiation (365 nm) for 15 minutes. The conversion was high (97%).

Figure 2:
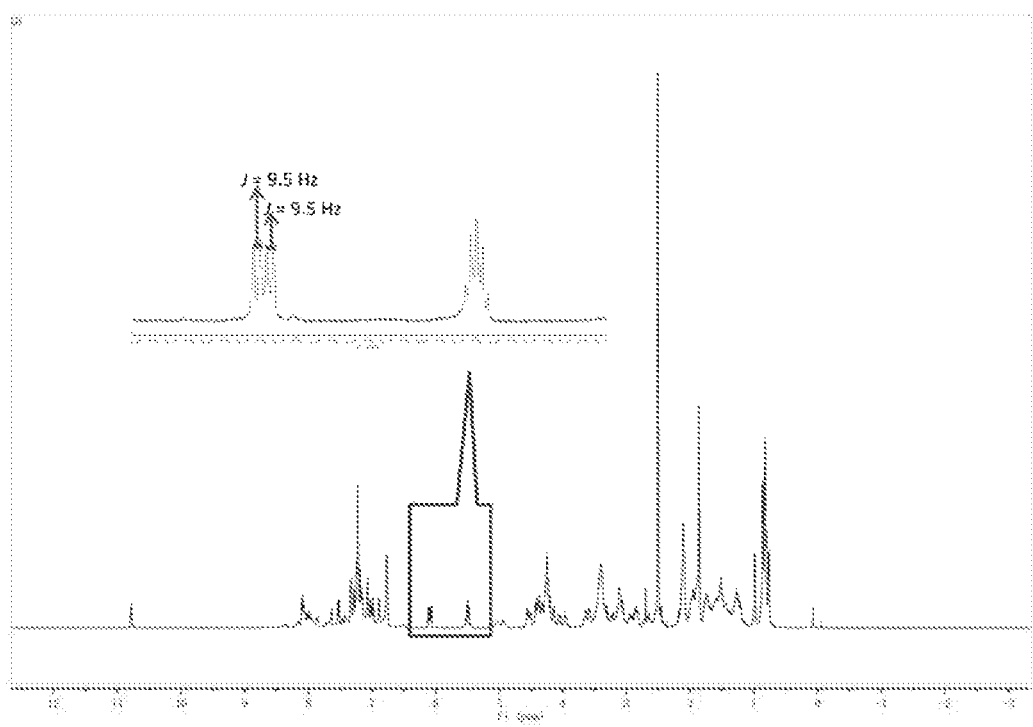
FIG. 2 shows $^1$H-NMR spectrum of ZZ isomer (at 500 MHz in DMSO-d$_6$).
Figure 3:
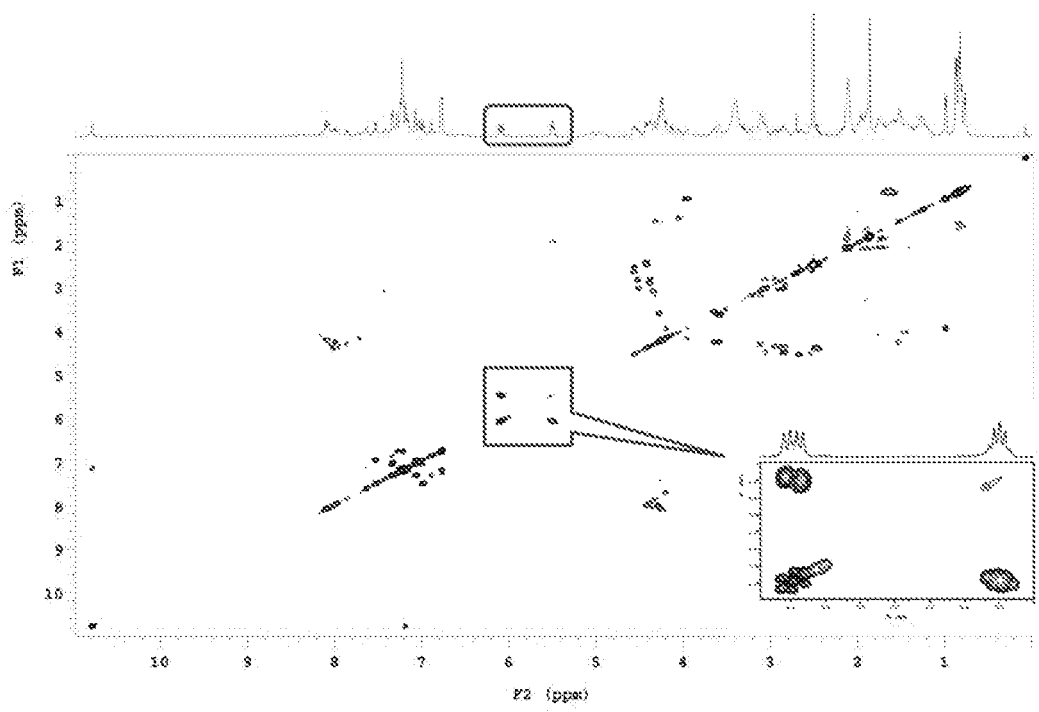
FIG. 3 shows Cosy spectrum of ZZ isomer (at 500 MHz in DMSO-d$_6$).
Figure 4:
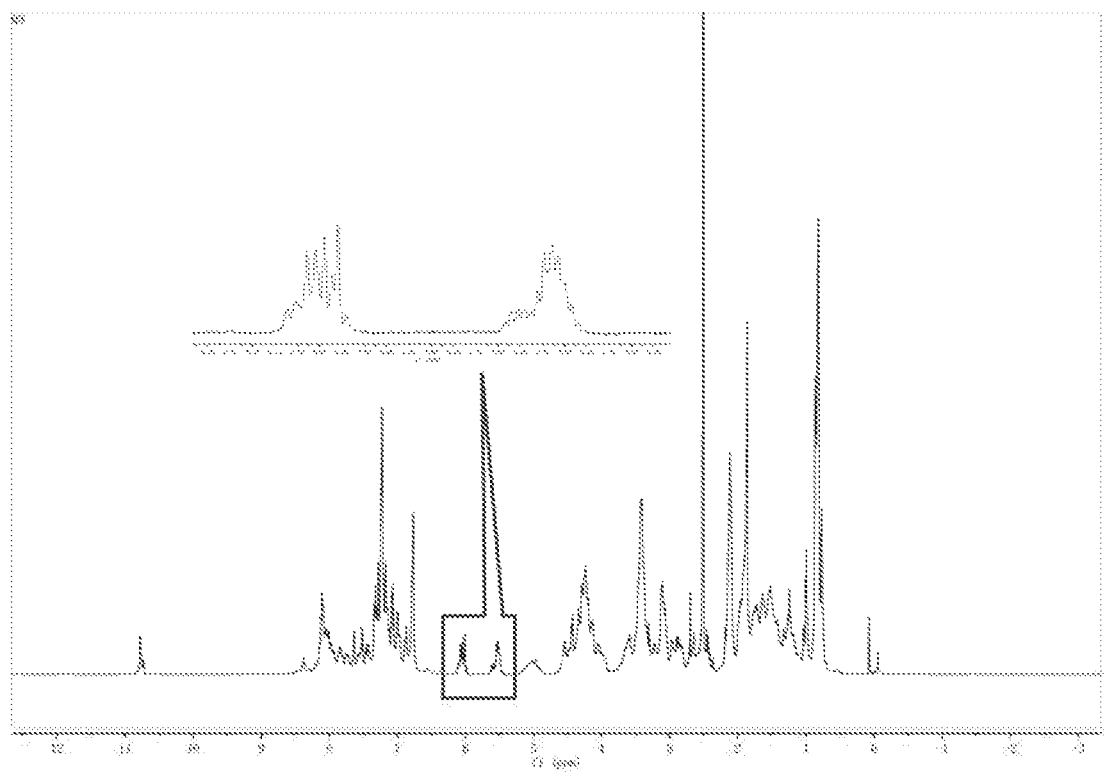
FIG. 4 shows $^1$H-NMR spectrum of left isomer (reaction by-product) (at 500 MHz in DMSO-d$_6$).
Figure 5:
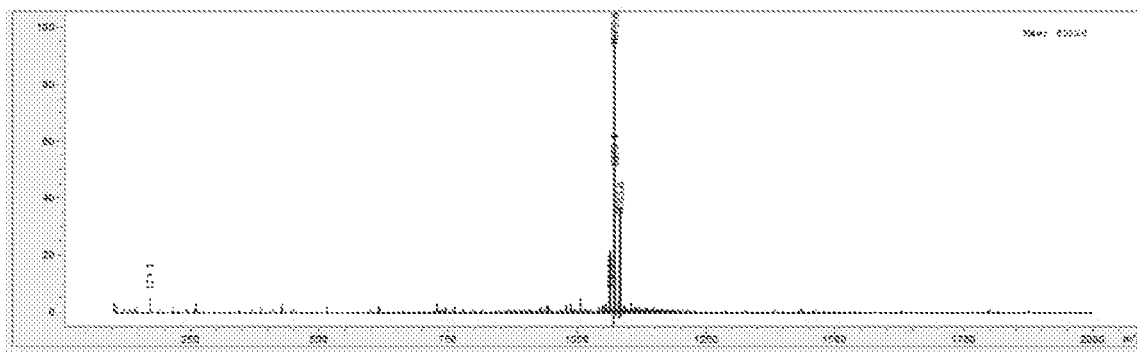
FIG. 5 shows MS-Spectrum for P-QSQ (p53 mimetic)+diyne.
Figure 6:
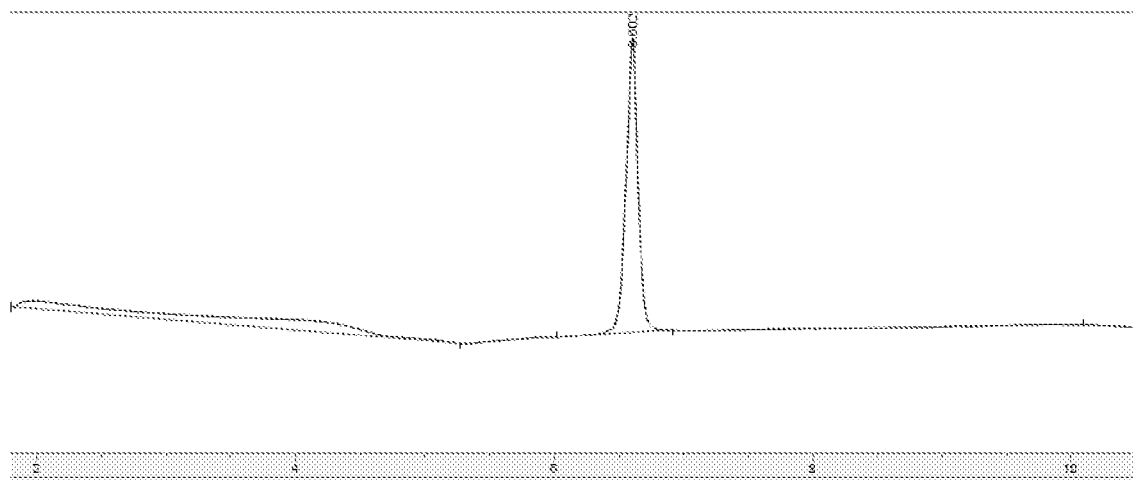
FIG. 6 shows LC-Chromatogram for P-QSQ (p53 mimetic)+diyne (ZZ isomer).
Figure 7:
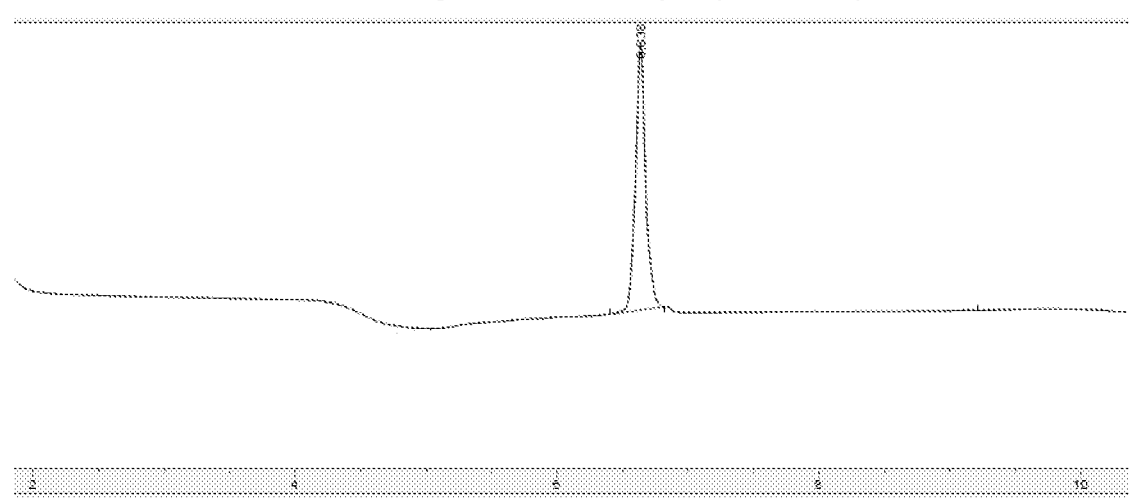
FIG. 7 shows LC-Chromatogram for P-QSQ (p53 mimetic)+diyne (left isomer).
Figure 8:
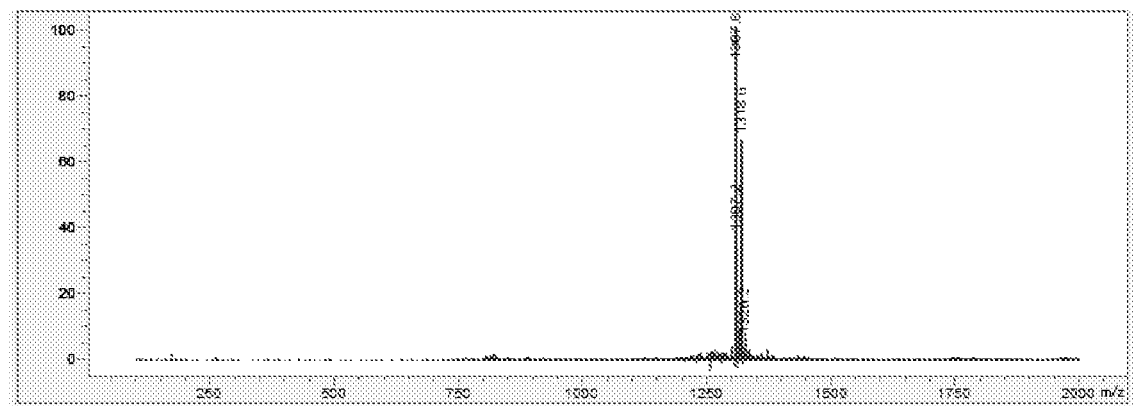
FIG. 8 shows MS-Spectrum for P-QSQ (p53 mimetic)+diyne+Cysteine.
Figure 9:
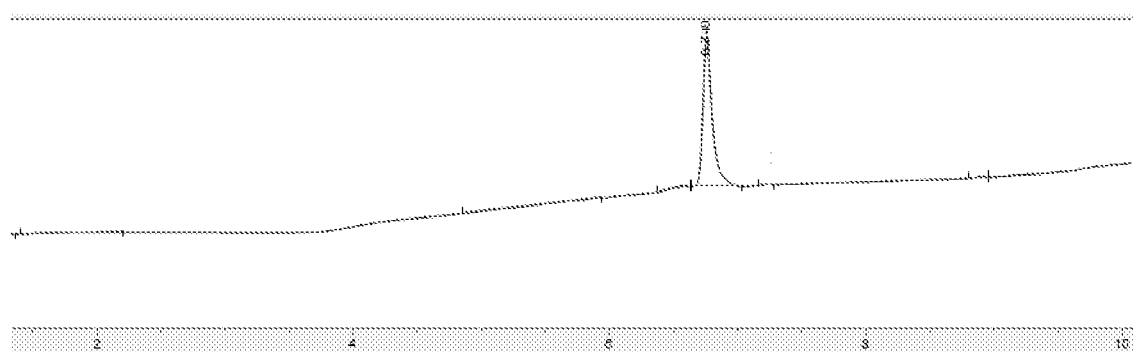
FIG. 9 shows LC-Chromatogram for P-QSQ (p53 mimetic)+diyne+Cysteine.
Figure 10:
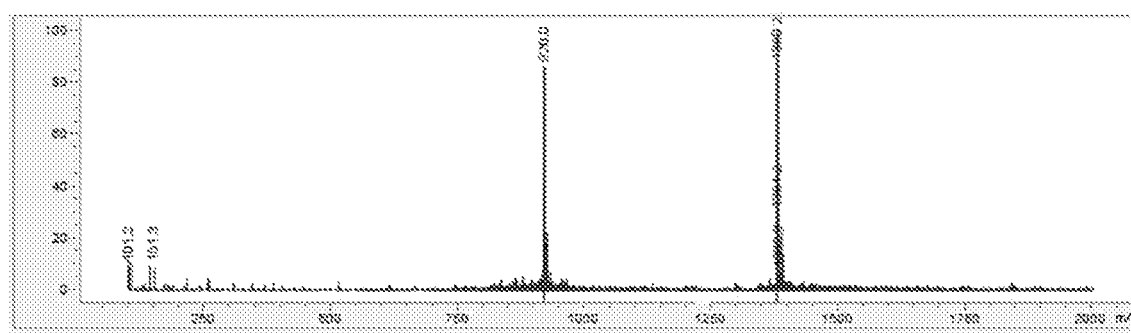
FIG. 10 shows MS-Spectrum for P-QSQ (p53 mimetic)+diyne+Glutathione.
Figure 11:
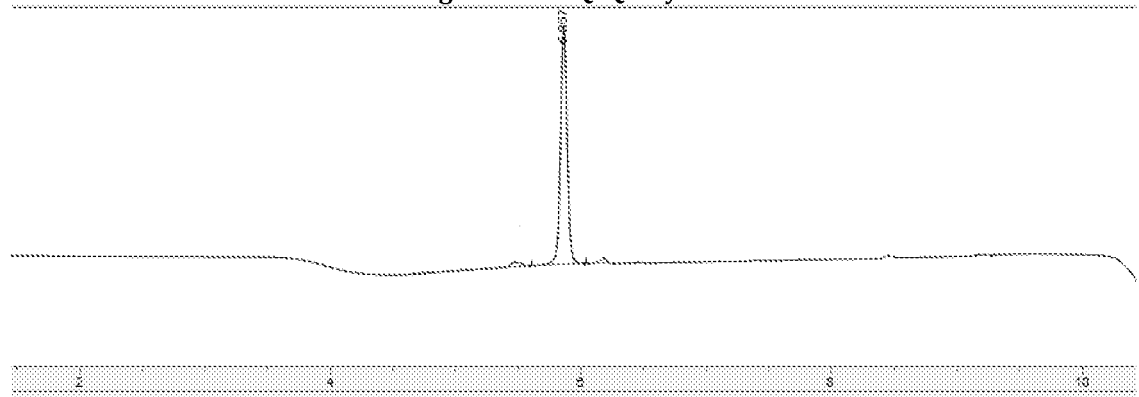
FIG. 11 shows LC-Chromatogram for P-QSQ (p53 mimetic)+diyne+Glutathione.

The product has two double bond and theoretically has four isomers: ZZ, ZE, EZ, EE. The conformations were assigned using $^1$H-NMR spectroscopy and 2D NMR spectra. See FIG. 2 and FIG. 3. Of the four different isomers, ZZ isomer was preferred with the percentage of 67%. Data is presented in FIG. 4, FIG. 5, FIG. 6, and FIG. 7.

5. Model Reaction

Using similar reaction conditions as in the previous example, Boc-protected cysteine and reduced glutathione were used as substrates to test the reactivity of the double bond respectively: (1 equiv), VA044 (1 equiv), TCEP (1 equiv), Boc-protected Cysteine or glutathione (5 equiv), hv, 365 nm, 15 min. Data is presented in FIG. 8, FIG. 9, FIG. 10, and FIG. 11.

6. Introducing CRRRRC to Stapled Peptide

Figure 12:
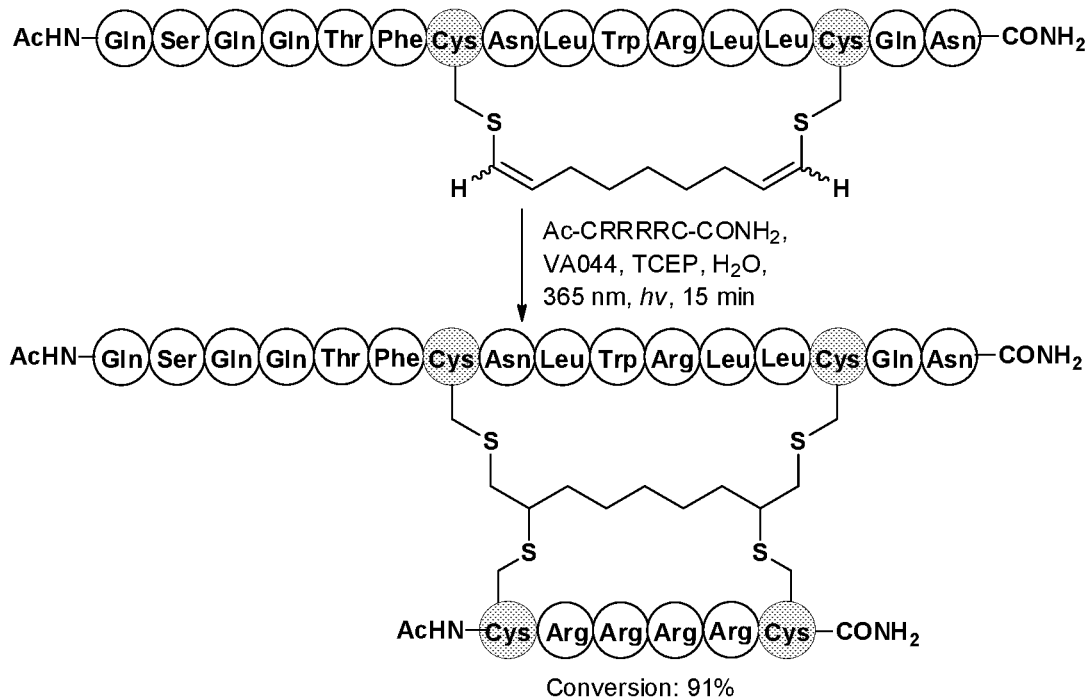
FIG. 12 shows a reaction schematic for introducing CRRRRC (cell-penetrating peptide) to stapled peptide.
Figure 13:
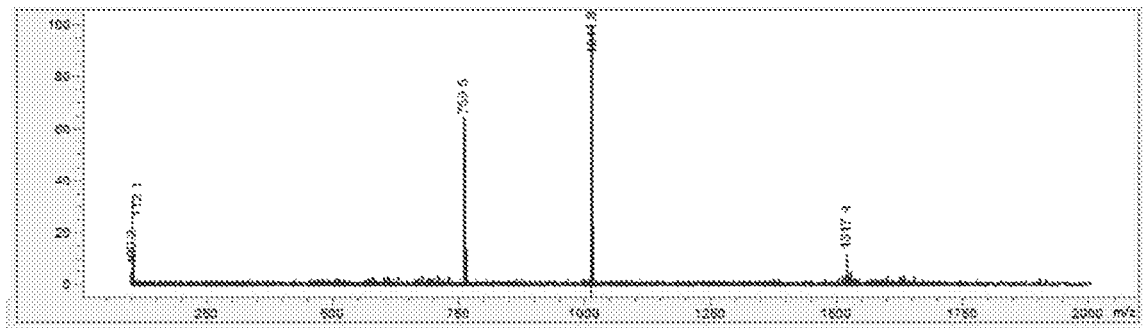
FIG. 13 shows MS-Spectrum for P-QSQ (p53 mimetic)+diyne+CRRRRC (cell-penetrating peptide).
Figure 14:
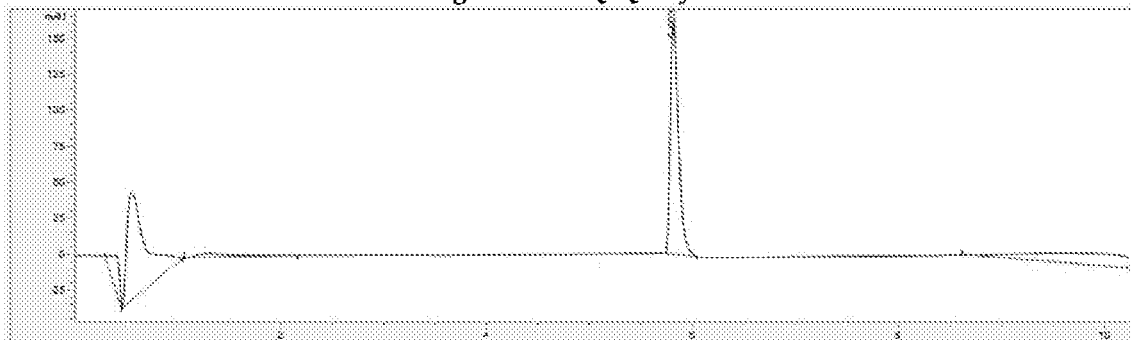
FIG. 14 shows LC-Chromatogram for P-QSQ (p53 mimetic)+diyne+CRRRRC (cell-penetrating peptide).

Using the reaction conditions from the previous example, the reaction was successful, and the conversion of 91%. VA044 (1 equiv), TCEP (1 equiv), CRRRRC (1 equiv), water, hv, 365 nm, 15 min. See FIG. 12. Data is presented in FIG. 13 and FIG. 14.

7. Introduction of FITC to P53 Mimetics

Figure 15:
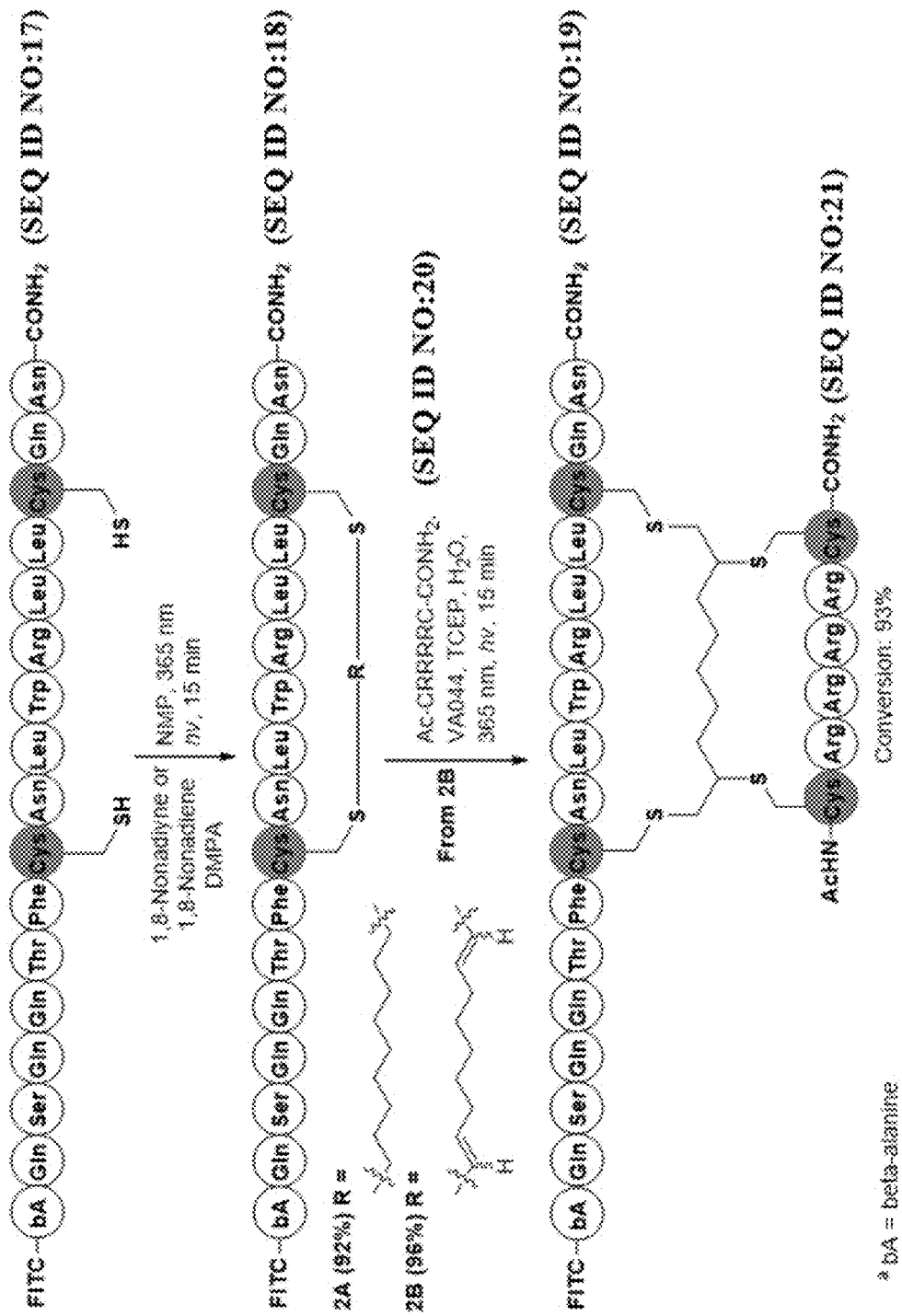
FIG. 15 shows a reaction schematic for introduction of FITC (fluorophore) to p53 mimetics.
Figure 16:
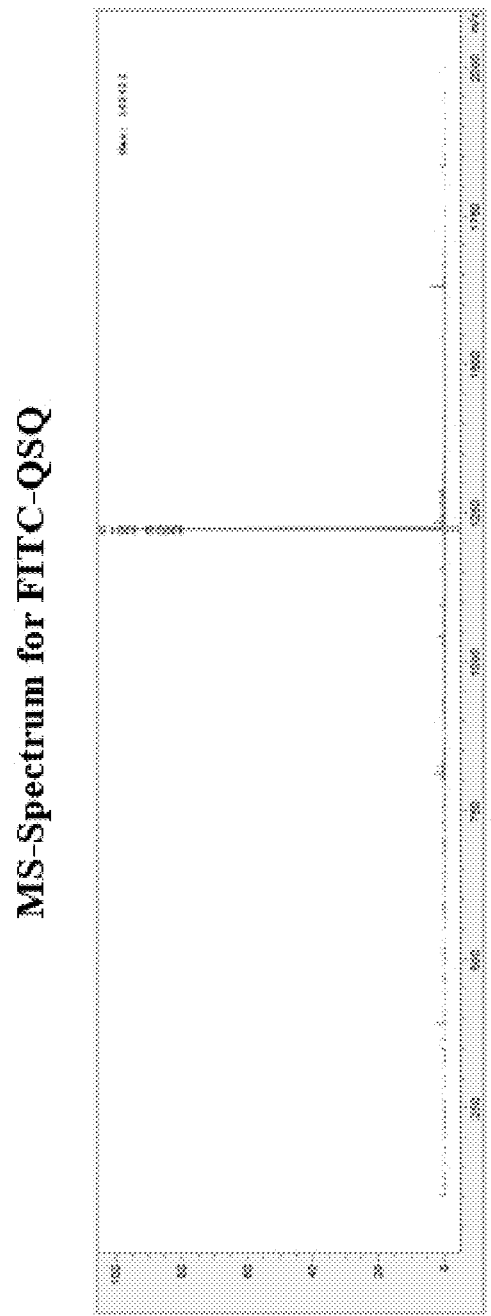
FIG. 16 shows MS-Spectrum for FITC-QSQ.
Figure 17:
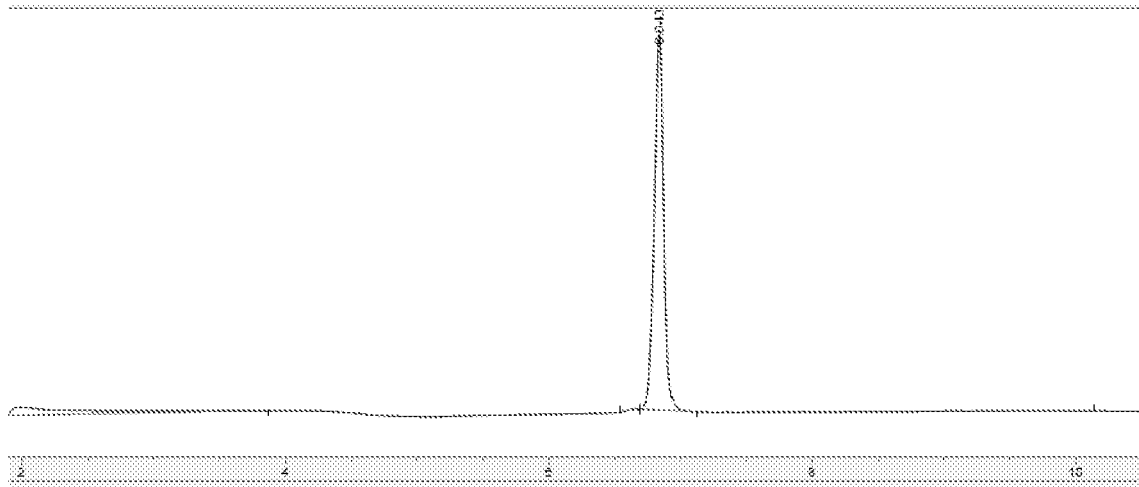
FIG. 17 shows LC-Chromatogram for FITC-QSQ.
Figure 18:
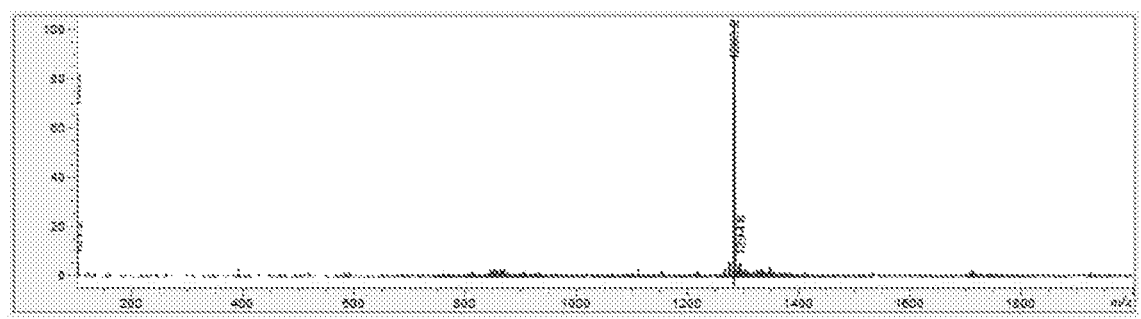
FIG. 18 shows MS-Spectrum for FITC-QSQ+1,8-diene.
Figure 19:
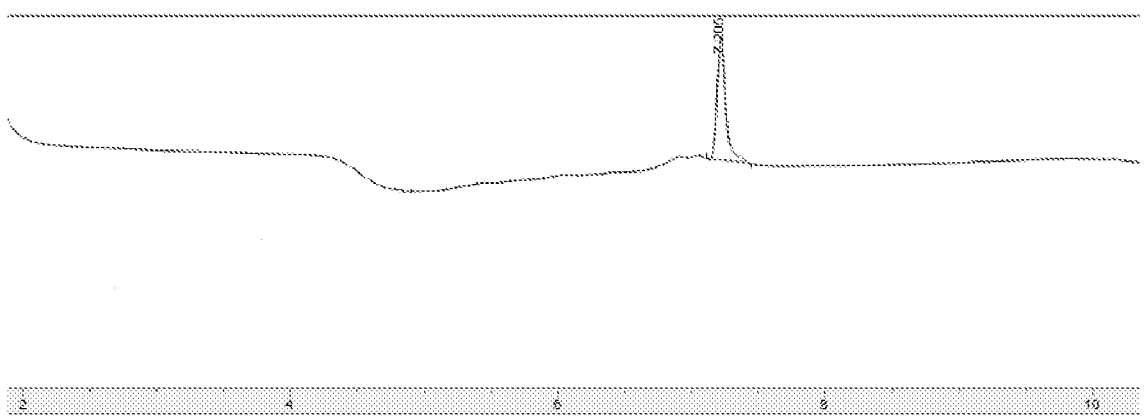
FIG. 19 shows LC-Chromatogram for FITC-QSQ+1,8-diene.
Figure 20:
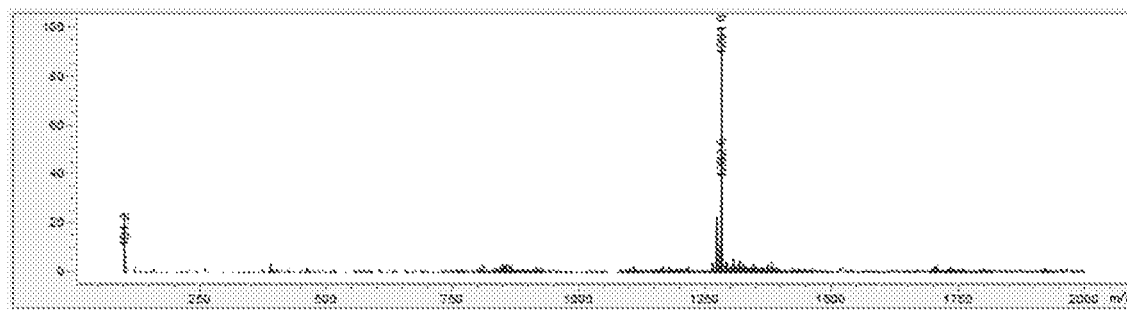
FIG. 20 shows MS-Spectrum for FITC-QSQ+diyne.
Figure 21:
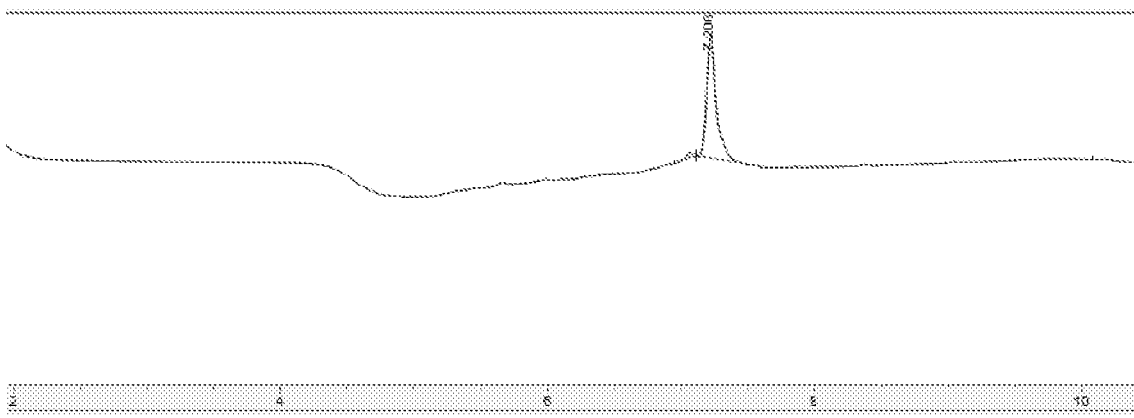
FIG. 21 shows LC-Chromatogram for FITC-QSQ+diyne.

For general reaction scheme, see FIG. 15. Step 1: Thiol-ene and/or thiol-yne reaction between FITC-QSQ and diene and/or diyne. The reaction conditions used were: FITC-QSS (1 eqiv), 1,8-Nonadiyne (1 equiv), DMPA (1 equiv), NMP, hv, 365 nm, 15 min, the conversion is 96%. Step 2: Introducing CRRRRC to stapled peptide. From the thiol-yne product (2B), one more step thiol-ene reaction was conducted, the reaction conditions used were: VA044 (1 equiv), TCEP (1 equiv), CRRRRC (1 equiv), water, hv, 365 nm, 15 min with the conversion of 93%. Data is presented in FIG. 16, FIG. 17, FIG. 18, FIG. 19, FIG. 20, and FIG. 21.

8. UCH37-RPN13 Inhibitors

Figure 22:
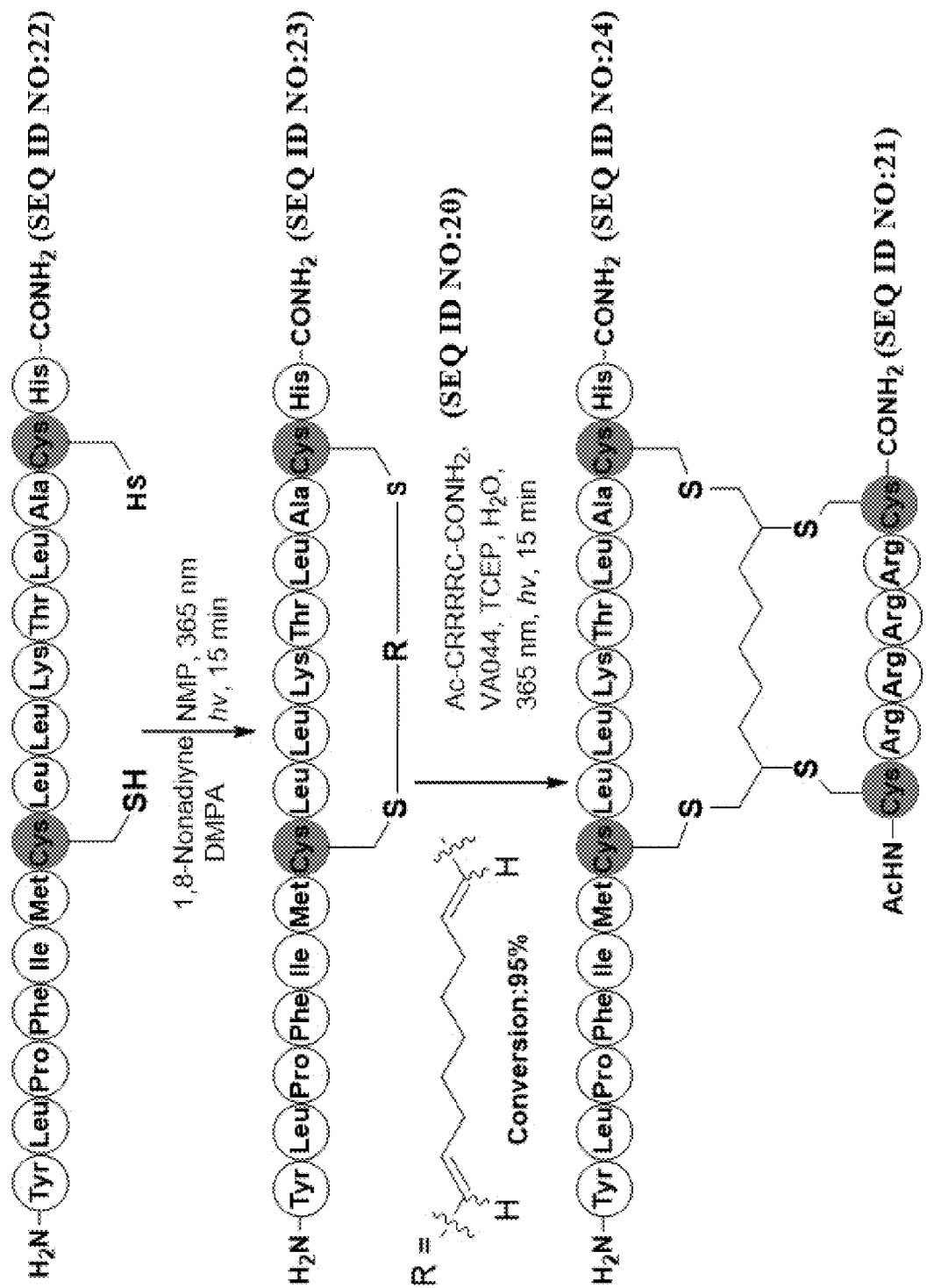
FIG. 22 shows a reaction schematic for UCH37-RPN13 inhibitors.
Figure 23:
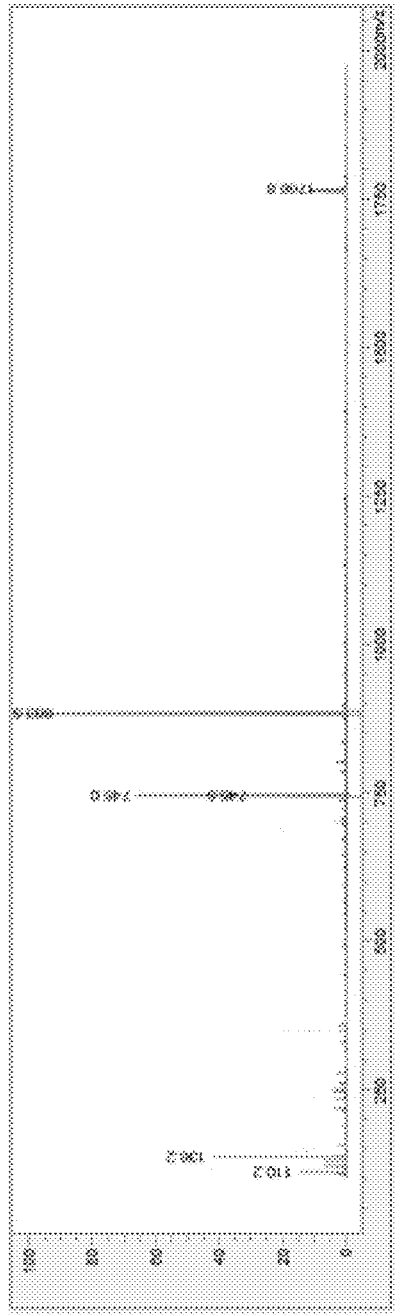
FIG. 23 shows MS-Spectrum for YLP (UCH37-RPN13 inhibitor).
Figure 24:
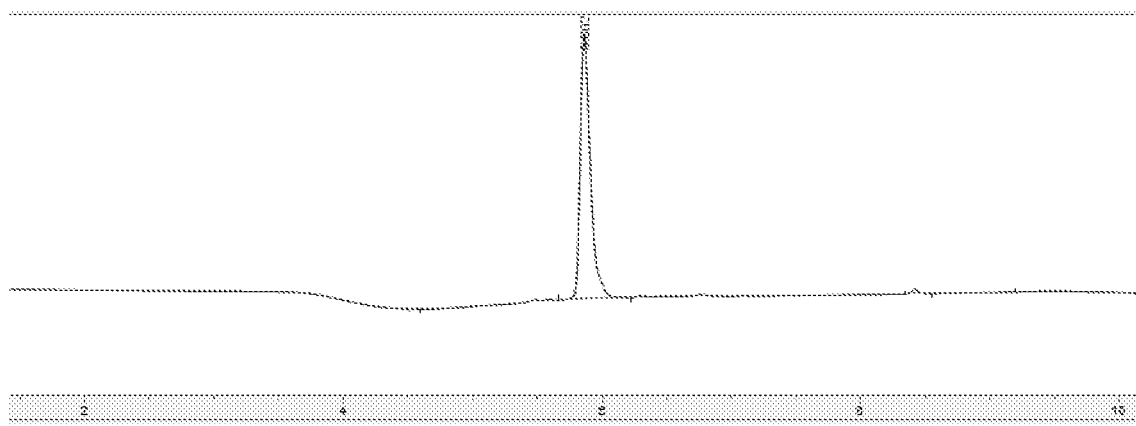
FIG. 24 shows LC-Chromatogram for YLP (UCH37-RPN13 inhibitor).
Figure 25:
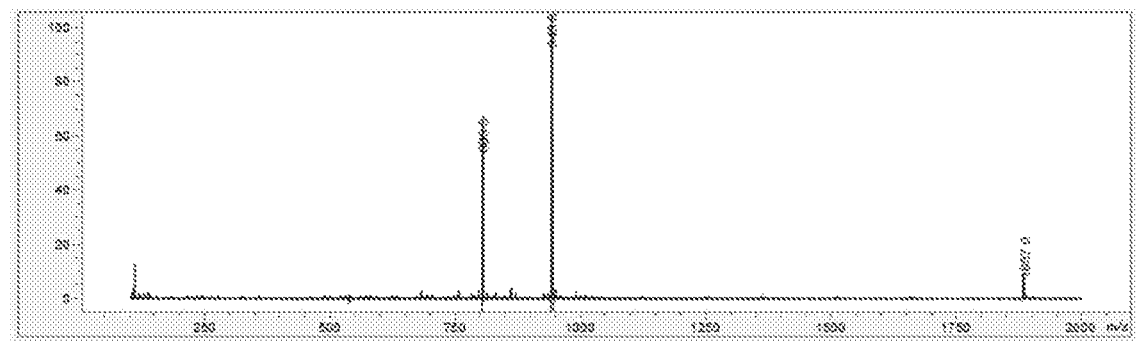
FIG. 25 shows MS-Spectrum for YLP (UCH37-RPN13 inhibitor)+diyne.
Figure 26:
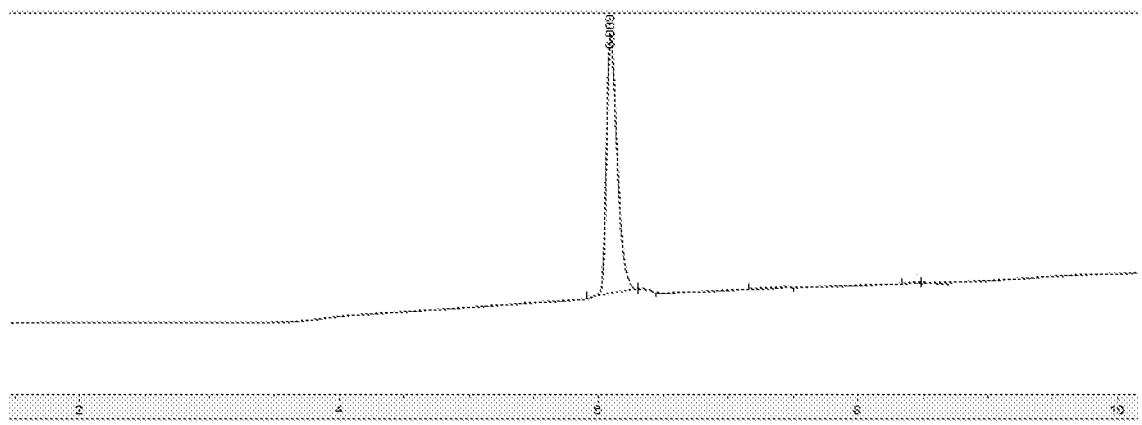
FIG. 26 shows LC-Chromatogram for YLP (UCH37-RPN13 inhibitor)+diyne.
Figure 27:
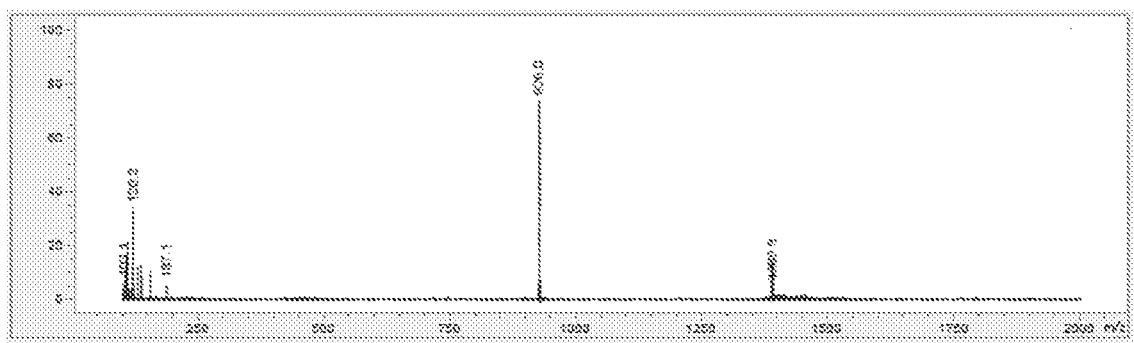
FIG. 27 shows MS-Spectrum for YLP (UCH37-RPN13 inhibitor)+diyne+CRRRRC (cell-penetrating peptide).
Figure 28:
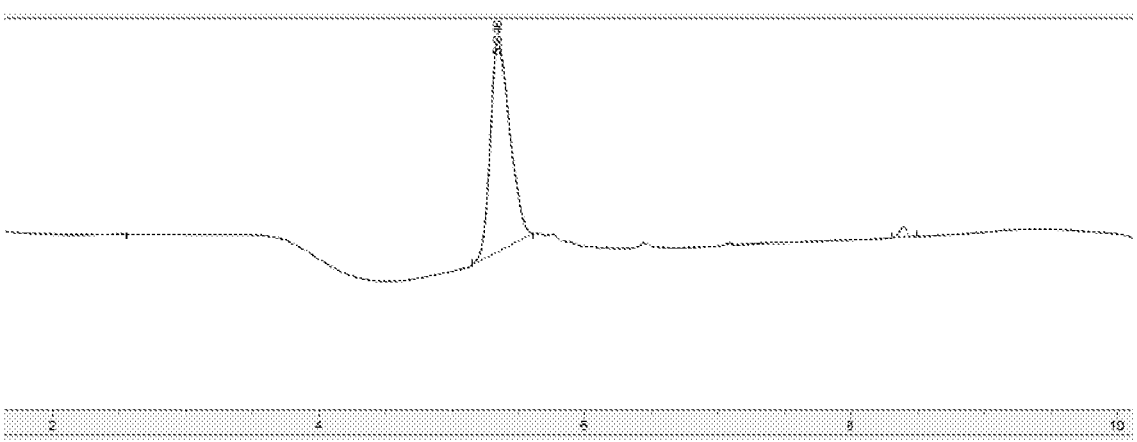
FIG. 28 shows LC-Chromatogram for YLP (UCH37-RPN13 inhibitor)+diyne+CRRRRC c.

For general reaction scheme, see FIG. 22. Data is presented in FIG. 23, FIG. 24, FIG. 25, FIG. 26, FIG. 27, and FIG. 28.

9. Cell-Penetrating P53 Mimetics

Figure 29:
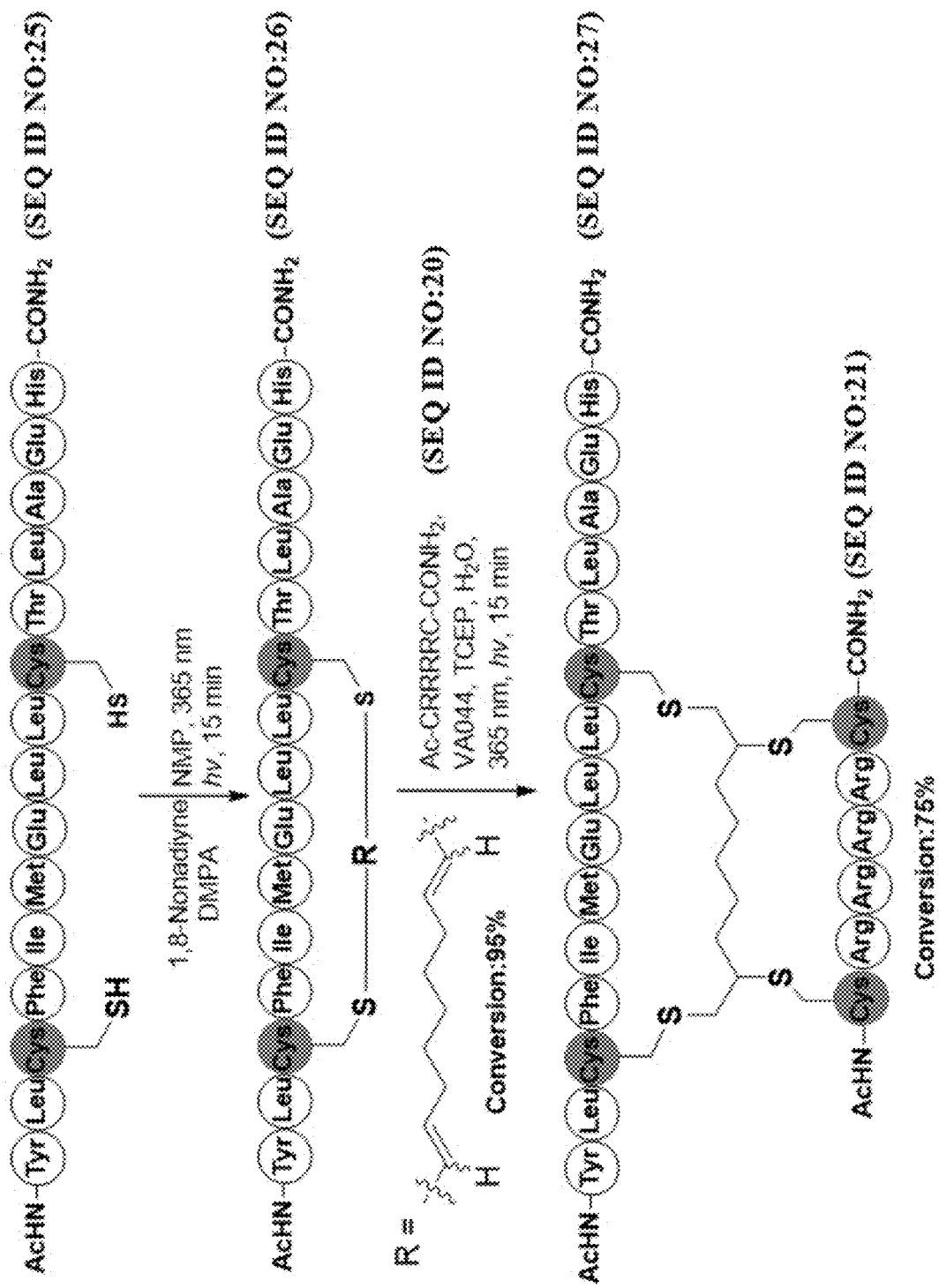
FIG. 29 shows Cell-penetrating p53 mimetics.
Figure 30:
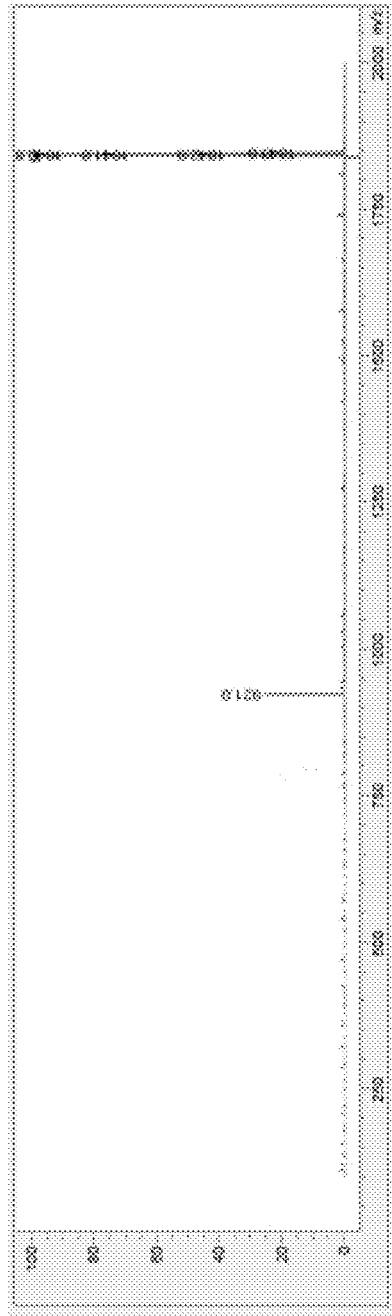
FIG. 30 shows MS-Spectrum for YLC (UCH37-RPN13 inhibitor).
Figure 31:
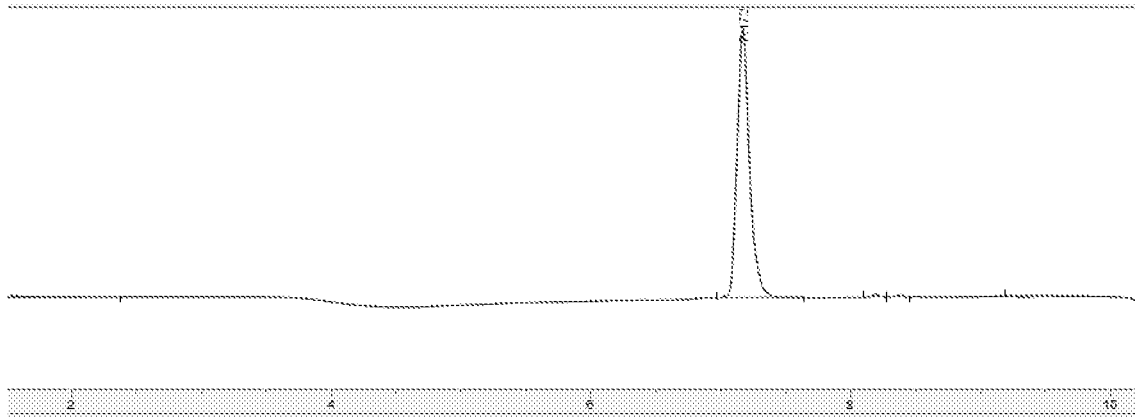
FIG. 31 shows LC-Chromatogram for YLC (UCH37-RPN13 inhibitor).
Figure 32:
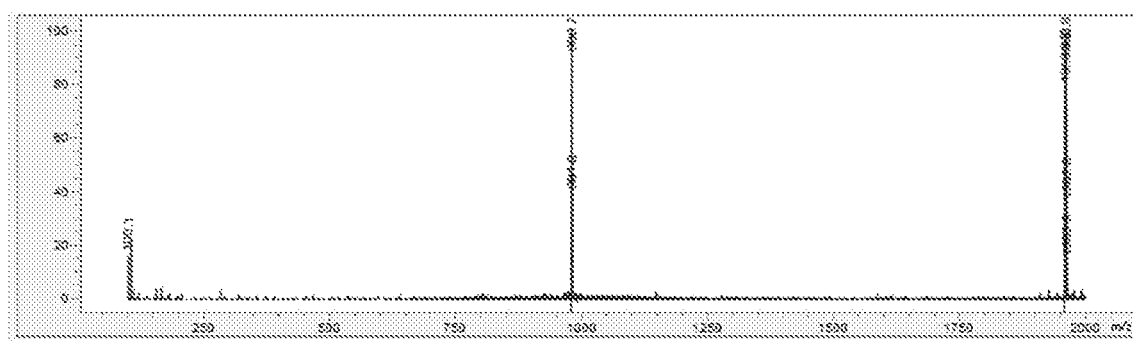
FIG. 32 shows MS-Spectrum for YLC (UCH37-RPN13 inhibitor)+diyne.
Figure 33:
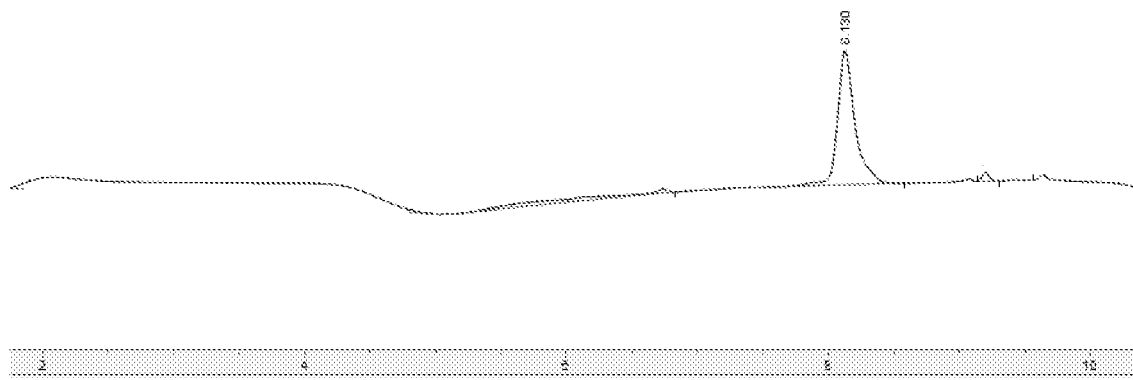
FIG. 33 shows LC-Chromatogram for YLC (UCH37-RPN13 inhibitor)+diyne.
Figure 34:
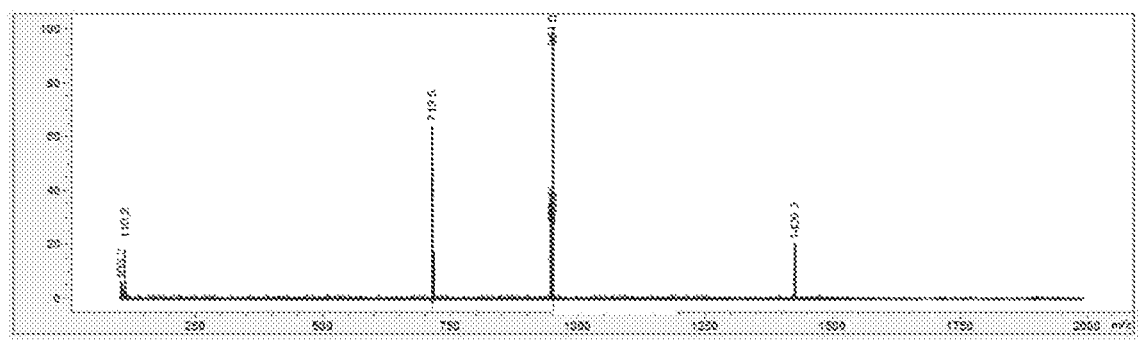
FIG. 34 shows MS-Spectrum for YLC (UCH37-RPN13 inhibitor)+diyne+CRRRRC (cell-penetrating peptide).
Figure 35:
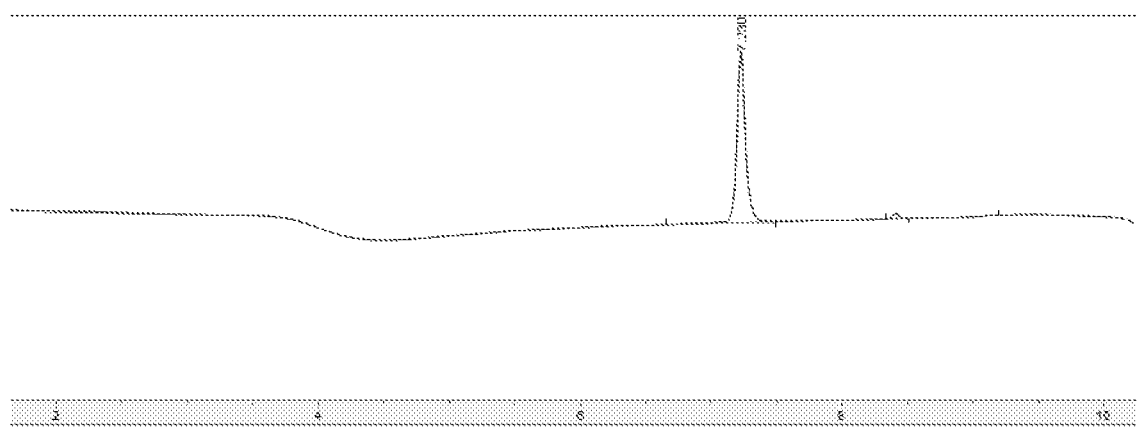
FIG. 35 shows LC-Chromatogram for YLC (UCH37-RPN13 inhibitor)+diyne+CRRRRC (cell-penetrating peptide).

For general reaction scheme, see FIG. 29. Data is presented in FIG. 30, FIG. 31, FIG. 32, FIG. 33, FIG. 34, and FIG. 35.

10. Internatlization of Stapled Peptides

Figure 36:
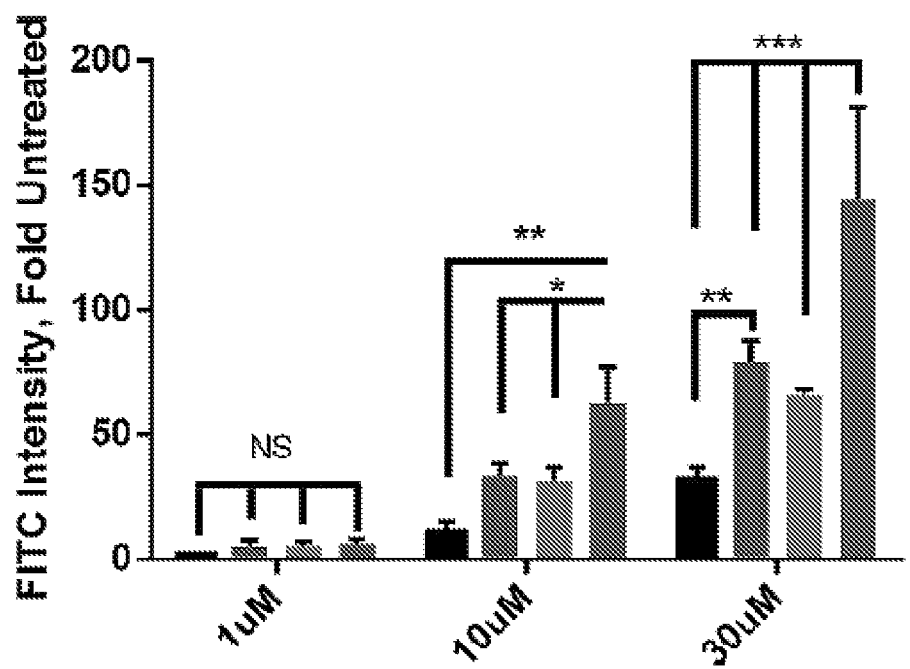
FIG. 36 shows the internalization of the starting peptide, 2A, 2B, and product peptide of FIG. 15 in K562 cells.

The internalization of the starting peptide, 2A, 2B, and the product peptide of FIG. 15 was tested (FIG. 36). At 1 μM concentrations, all four peptide analogues showed no significant internalization by the cell lines. At 10 and 30 μM concentrations, the modified product peptide was internalized far better than the others. Both stapled pepts 2A and 2B had improved internalization compared to the unstapled starting peptide; however, the difference between the two was not significant.

Referring to FIG. 36, the internalization of the starting peptide, 2A, 2B, and product peptide of FIG. 15 in K562 cells is shown (from left to right at each concentration: starting peptide, 2A, 2B, and product peptide). The bicyclic product peptide demonstrated superior internalization compared to all other peptides at 10 and 30 μM doses. 2-way ANOVA with Tukey's multiple comparison test; n=3; *p<0.05; p<0.001; *p<0.0001.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of preparing a stapled peptide, the method comprising the steps of:

a) providing a peptide having the structure represented by the formula:

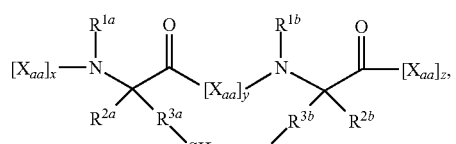

wherein each of x and z is independently an integer having a value of 0 to 100;

wherein y is an integer having a value of 1 to 20;

wherein each instance of $X_{aa}$ is, independently, a natural or unnatural amino acid;

wherein each of $R^{1a}$ and $R^{1b}$ is independently hydrogen or an amino protecting group;

wherein each of $R^{2a}$ and $R^{2b}$ is independently hydrogen or C1-C4 alkyl;

wherein each of $R^{3a}$ and $R^{3b}$ is independently a C1-C4 alkyl;

b) providing a linker compound having the structure represented by the formula:

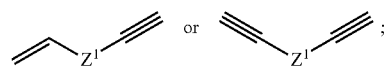

wherein $Z^1$ is C1-C8 alkyl, C3-C8 ether, C6-C8 polyether, or a moiety represented by a formula:

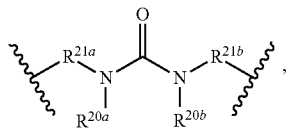

wherein each of $R^{20a}$ and $R^{20b}$ is independently selected from hydrogen and C1-C4 alkyl; and
wherein each of $R^{21a}$ and $R^{21b}$ is independently C3-C6 alkylene;
or a moiety represented by a formula:

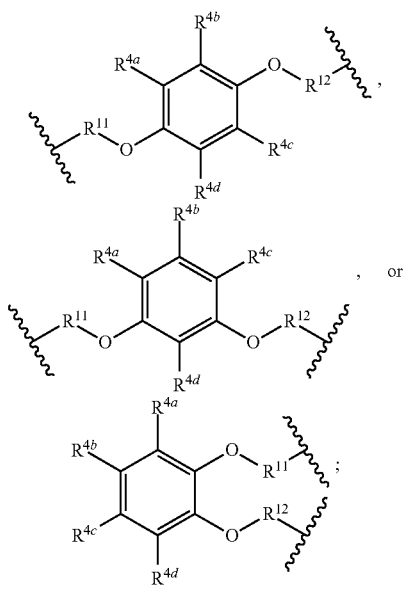

wherein each of $R^{4a}$, $R^{4b}$, $R^{4c}$, and $R^{4d}$ is independently hydrogen, hydroxy, amino, C1-C4 alkyl, and —$CO_2H$; and
wherein each of $R^{11}$ and $R^{12}$ is independently C1-C4 alkyl;
c) reacting the peptide and the linker compound;
thereby forming the stapled peptide.

2. The method of claim 1, wherein the reaction is performed in the presence of a radical initiator.

3. The method of claim 1, wherein each of $R^{3a}$ and $R^{3b}$ is —$CH_2$—.

4. The method of claim 1, wherein $Z^1$ is a moiety represented by a formula:

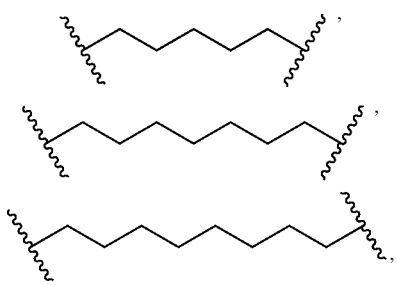

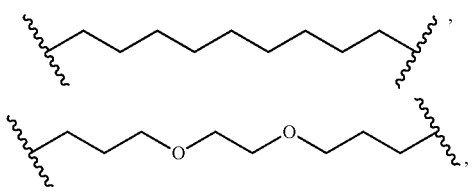

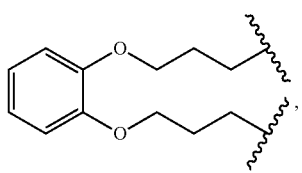

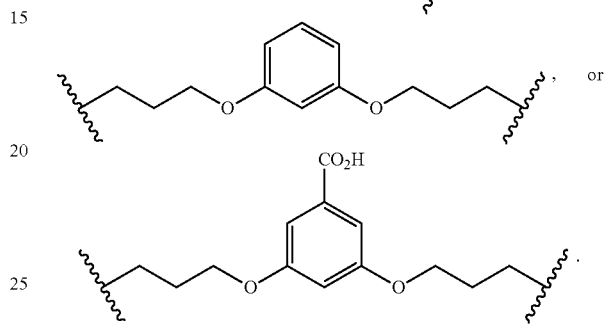

, or

5. The method of claim 1, wherein the linker compound has a structure represented by a formula:

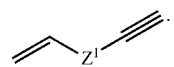

6. The method of claim 1, wherein the linker compound has a structure represented by a formula:

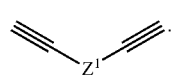

7. The method of claim 1, wherein the peptide contains all natural residues.

8. The method of claim 1, wherein reacting is via a free-radical reaction.

9. The method of claim 1, wherein the stapled peptide has a structure represented by a formula:

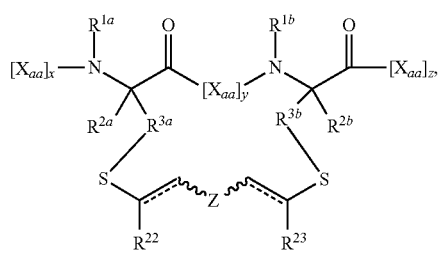

wherein each occurrence of ---- is an optional covalent bond, thereby signifying a single bond or a double bond.

10. The method of claim 9, wherein the stapled peptide has a structure represented by a formula:

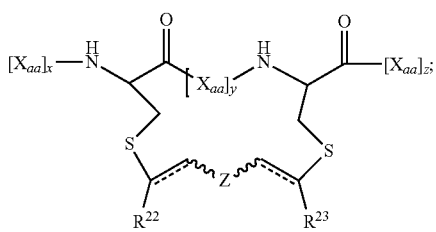

wherein each of x and z is independently an integer having a value of 2 to 15;
wherein y is 2, 3, 6 or 10; and
wherein Z is a moiety represented by a formula:

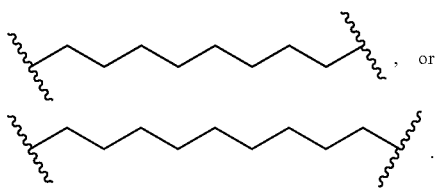

11. The method of claim 9, wherein at least one occurrence of --- is a covalent bond, thereby signifying a double bond.

12. The method of claim 11, further comprising reacting the double bond with a radical agent or a nucleophilic agent.

13. The method of claim 12, wherein the radical agent comprises a thiol.

14. The method of claim 12, wherein the radical agent comprises a solubilizing functionality, a labeling functionality, a tether to solid-phase support, or a tether to a second peptide.

15. The method of claim 12, wherein the nucleophilic agent comprises an alcohol or an amine.

16. The method of claim 12, wherein the nucleophilic agent comprises a solubilizing functionality, a labeling functionality, a tether to solid-phase support, or a tether to a second peptide.

17. The method of claim 1, wherein the peptide comprises the sequence (SEQ ID NO: 1)
HSQGTFTSDYSKYLDSCRAQCFVQWLMNT, (SEQ ID NO: 2)
HSQGTFTSDYSKYLDSRRACDFVCWLMNT, (SEQ ID NO: 3)
HSQGTFTSDYSKYLDSRRACDFVQWLCNT, (SEQ ID NO: 4)
HSQGTFTSDYSKYLDSRRAQCFVQWLMCT,
or (SEQ ID NO: 5)
HSQGTFTSDYSKYLDSRRAQDFVCWLMCT.

18. The method of claim 17, wherein the stapled peptide has a structure represented by a formula:

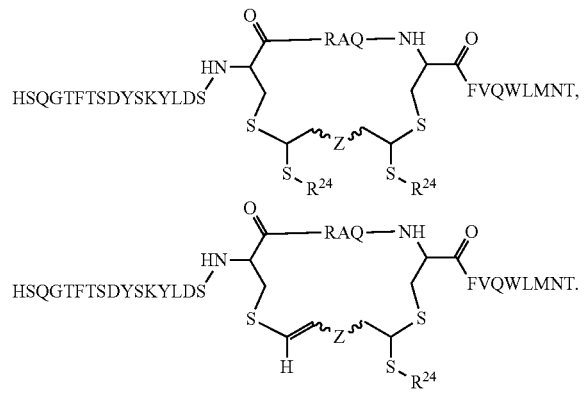

* * * * *